(12) United States Patent
Nielsen et al.

(10) Patent No.: US 7,064,118 B2
(45) Date of Patent: Jun. 20, 2006

(54) HETEROARYL DIAZACYCLOALKANES, THEIR PREPARATION AND USE

(75) Inventors: Simon Feldbaek Nielsen, Herlev (DK); Dan Peters, Malmo (SE); Elsebet Ostergaard Nielsen, Kobenhavn K (DK); Gunnar M. Olsen, Frederiksberg (DK)

(73) Assignee: Neurosearch A/S, Ballerup (DK)

( * ) Notice: Subject to any disclaimer, the term of this patent is extended or adjusted under 35 U.S.C. 154(b) by 597 days.

(21) Appl. No.: 09/934,531

(22) Filed: Aug. 23, 2001

(65) Prior Publication Data

US 2002/0045618 A1    Apr. 18, 2002

Related U.S. Application Data

(63) Continuation of application No. PCT/DK00/00202, filed on Apr. 19, 2000.

(30) Foreign Application Priority Data

Apr. 26, 1999  (DK) ............... 1999 00571
Oct. 20, 1999  (DK) ............... 1999 01504

(51) Int. Cl.
*A16P 25/00*   (2006.01)
*A16K 31/495*  (2006.01)
*C07D 403/00*  (2006.01)

(52) U.S. Cl. ....................... 514/218; 540/575
(58) Field of Classification Search ............... 514/218; 540/575

See application file for complete search history.

(56) References Cited

U.S. PATENT DOCUMENTS

| | | | |
|---|---|---|---|
| 4,025,617 A * | 5/1977 | Green et al. ............. | 424/78.32 |
| 4,163,849 A | 8/1979 | Lumma, Jr. et al. ........ | 544/357 |
| 4,179,563 A | 12/1979 | Butler ..................... | 544/360 |
| 4,639,415 A * | 1/1987 | Kaneko et al. ............ | 430/558 |
| 4,806,536 A | 2/1989 | Cross et al. ............. | 514/252 |
| 6,448,242 B1 * | 9/2002 | Ishiwata et al. ......... | 514/210.18 |

FOREIGN PATENT DOCUMENTS

| | | |
|---|---|---|
| EP | A215643 3 | 10/1985 |
| EP | A221145 7 | 2/1987 |
| EP | A2361489 | 4/1990 |
| EP | A138535 0 | 9/1990 |
| EP | A180217 3 | 10/1997 |
| GB | 1492528 | 11/1977 |
| WO | A19610568 | 4/1996 |
| WO | A1992183 4 | 5/1999 |
| WO | WO 99/42446 * | 8/1999 |

OTHER PUBLICATIONS

Schmitt et al., Targeting Nicotinic Acetylcholine Receptors: Advances in Molecular Design and Therapies, Annual Reports in Medicinal Chemistry, vol. 35, pp. 41-51, 2000.*
Xu et al., Sch. Pharm. Sci., vol. 23, No. 6, pp. 477-480 (1991) Abstract.
Manetti et al., Bioorganic and Medicinal Chemistry, vol. 7, pp. 457-465 (1999).
Georgiev et al., Med. Akad., vol. 27, No. 3, pp. 23-28 (1977) Abstract.
Nielsen et al., J. Med. Chem, vol. 43, pp. 2217-2226 (2000).

* cited by examiner

*Primary Examiner*—Brenda Coleman
(74) *Attorney, Agent, or Firm*—Birch, Stewart, Kolasch & Birch, LLP

(57) ABSTRACT

The present invention relates to novel heteroaryl diazacycloalkane derivatives which are found to be cholinergic ligands at the nicotinic Acetyl Choline Receptors. Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

7 Claims, No Drawings

HETEROARYL DIAZACYCLOALKANES, THEIR PREPARATION AND USE

This application is a Continuation of PCT International Application No. PCT/DK00/00202 filed on Apr. 19, 2000, which was published in English and which designated the United States and on which priority is claimed under 35 U.S.C. §120, the entire contents of which are hereby incorporated by reference.

The present invention relates to novel heteroaryl diazacycloalkane derivatives which are found to be cholinergic ligands at the nicotinic acetyl choline receptors.

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetyl choline receptors dominate quantitatively over nicotinic acetyl choline receptors in the brain area important to memory and condition, and much research aimed at the development of agents for the treatment of memory related disorders have focused on the synthesis of muscarinic acetyl choline receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel nicotinic receptor modulators, which modulators are useful for the treatment of diseases or disorders related to the cholinergic receptors, and in particular the nicotinic acetyl choline receptor (nAChR).

Due to their pharmacological profile the compounds of the invention may be useful for the treatment of diseases or disorders as diverse as those related to the cholinergic system of the central nervous system (CNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazacycloalkane derivatives represented by the general Formula I

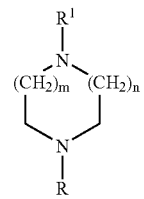

or a dimeric compound thereof represented by either of Formulae II, III or IV

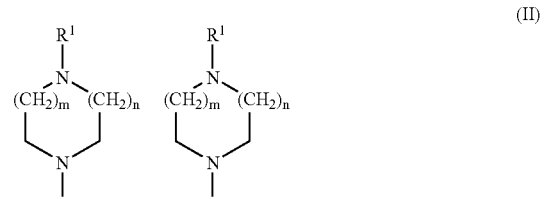

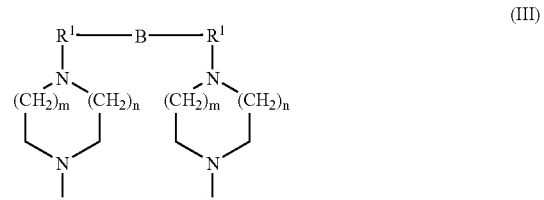

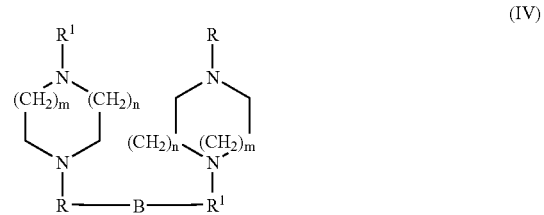

any of its enatiomers or any mixture thereof, an N oxide thereof, a pharmaceutically acceptable salt thereof, in a labelled or un-labelled form, wherein, n is 1, 2 or 3; and m is 0, 1 or 2; and R represents hydrogen, an alkyl group, a cycloalkyl group, a cycloalkylalkyl group, an alkenyl group, an alkynyl group, an aralkyl group, an alkoxypyridyl group, or an alkenoxypyridyl group; or "—R—B—R—" in Formula II represents a single bond bridge ("—", i.e. R and B are absent), or a bridgin group of the formula "R—R—" (i.e. B is absent) or a bridging group of the formula "—R—" (i.e. R is absent in only one of the two compounds making up the dimeric substance); or "R—R—R$^1$" in Formula IV represents a single bond bridge ("—", i.e. R, B and R$^1$ are absent), or a bridging group of the formula "R—R$^1$—" (i.e. B is absent); or "R—B" in Formula IV represents a single bond bridge ("—", i.e. R and B are absent, R$^1$ is present); or R and R$^1$ are identical and represent a monocyclic 5 to 6 membered heterocyclic group, which heterocyclic group may be substituted one or more times with alkyl, alkoxy, cycloalkyl, cycloalkoxy, alkoxycycloalkyl, cycloalkoxyalkoxy, cycloalkylalkyl, hydroxyalkyl, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifuluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, —NH—CO$_2$R$^2$, —NHCO—R$^2$ or —OCO—NR$^2$R$^3$; in which formulae R$^2$ and R$^3$ independently of each another represents hydrogen or alkyl; and R$^1$ represents a monocyclic 5 to 6 membered heterocyclic group, which heterocyclic group may be substituted one or more times with alkyl, alkoxy, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, —NH—CO$_2$R$^2$, —NHCO—R$^2$ or —OCO—NR$^2$R$^3$; in which formulae R$^2$ and R$^3$ independently of each another represents hydrogen or alkyl; or which heterocyclic group may be substituted with an aryl group, which aryl group may optionally be substituted one or more times with alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which heterocyclic group may be substituted with a group of the formula "—X-alkyl-Y-alkyl", in which formula X and Y independently of each another represent O (epoxy), S, NH, N-alkyl, or Se; and alkyl is optionally substituted with alkoxy, or alkylthio; or which heterocyclic group may be substituted with a group of the formula "—X-(ALK)$_o$aryl", in which formula X represents O, S, NH, N-alkyl or Se; "ALK" represents alkyl, alkenyl or alkynyl; aryl is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; and o is 0 or 1; or which heterocyclic group may be substituted with a group of the formula "—X—(ALK)$_o$—Z", in which formula "ALK" represents alkyl, alkenyl or alkynyl; X represents O, S, NH, N-alkyl or Se; Z represents a 5- or 6-membered monocyclic heterocyclic group, which heterocyclic group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; and o is 0 or 1; or which heterocyclic group may be substituted with another monocyclic 5 to 6 membered heterocyclic group, which additional heterocyclic group may be substituted one or more times with alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which heterocyclic group may be substituted with a group of the formula "(ALK)$_o$-HET", in which formula "ALK" represents alkyl, alkenyl or alkynyl; o is 0 or 1; and HET represents a non-aromatic heterocyclic group; or or R$^1$ represents a bicyclic heterocyclic group, which bicyclic group is composed of a 5 to 6 membered monocyclic heterocyclic group fused to a benzene ring, which bicyclic group may be substituted one or more times with alkyl, alkoxy, alkoxy-alkoxy, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, —NH—CO$_2$R$^2$, —NHCO—R$^2$ or —OCO—NR$^2$R$^3$; in which formulae R$^2$ and R$^3$ independently of each another represents hydrogen or alkyl; or which bicyclic group may be substituted with an aryl group, which aryl group is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which bicyclic group may be substituted with an additional monocyclic 5 to 6 membered heterocyclic group, which additional heterocyclic group is optionally substituted one or more times with alkyl, cycloalkyl, cycloalkylalkyl alkenyl, alkynyl, In the context of this invention a cycloalkyl group designates a cyclic alkyl group, preferably containing of from three to seven carbon atoms (C$_{3-7}$-cycloalkyl), including cyclopropyl, cyclobutyl, cyclopentyl, cyclohexyl and cycloheptyl.

In the context of this invention oa cycloalkyl-alkyl group designates a cycloalkyl group as defined above, which cycloalkyl gorup is substituted on an alkyl group as also define above. Examples of preferred cycloalkyl-alkyl groups of the invention include cyclopropylmethyl and cyclopropylethyl.

In the context of this invention an alkoxy group designates an "alkyl-O-" gorup, wherien alkyl is as defined above, an alkenoxy group designates an "alkenyl-O-" group, wherein alkenyl is as defined above, and a cycloalkoxy group designates a "cycloalkyl-O-" group, wherein cycloalkyl is as defined above.

In the context of this invention an alkylthio group designates an "alkyl-S-" group (thioalkoxy), wherein alkyl is as defined above, an alkenylthio group designates an "alkenyl-S-" group, wherein alkenyl is as defined above, and an alkynylthio group designates an "alkynyl-S-" group, wherein alkynyl is as defined above. Likewise an arylthio group designates an "aryl-S-" group, wherein aryl is as defined below, and an arylalkylthio designates an "arylalkyl-S-" group, wherein arylalkyl is as defined below, alkylthioalkoxy, alkoxy-alkylthio, and alkylthio-alkylthio-alkylthio designates an alkylthio group as defined above, attached to another alkylthio group, or to an alkoxy group as defined above.

In the context of this invention an alkylseleno group designates an "alkyl-Se-" group, wherien alkyl is as defined above, an alkenylseleno designates an "alkenyl-Se-" group, wherien alkenyl is as defined above, and an alkynylseleno group designates an "alkynyl-Se-" group, wherein alkynyl is as defined above.

In the context of this invention an alkyloxime group designates a "C═N—O-alkyl" group, wherein alkyl is as defined above, and an acyloxime group designates a "C═N—O—COOH" group or a "C═N—O—CO-alkyl" group, wherein alkyl is as defined above.

In the context of this invention an amino group may be a primary (—NH$_2$), secondary (—NH-alkyl), or tertiary (—N (alkyl)$_2$) amino group, i.e. it may be substituted once or twice with an alkyl group as defined above.

In the context of this invention aryl designates a mono- or polycyclic aryl group, i.e. a monocyclic or polycyclic aromatic hydrocarbon group. Examples of preferred aryl groups of the invention include phenyl, naphthyl, indenyl, azulenyl, anthracenyl, and fluorenyl.

In the context of this invention an aralkyl group designates a mono- or polycyclic aryl group as defined above, which aryl gorup is attached to an alkyl group as also define above. Examples of preferred aralkyl groups of the invention include benzyl, and phenethyl. alkoxy, cycloalkoxy, alkenoxy, alkynoxy, methyleneodioxy, halogen, —OH, —CF$_3$, —OCF$_3$, —CN, amino, nitro, oxime, alkyloxime, acyloxime; or "—R$^1$—B—R$^1$—" in Formula III represents a single bond bridge ("—", i.e. R$^1$ and B are absent), or a bridging group of the formula "R$^1$—R$^1$—" (i.e. B is absent), or a bridging group of the formula "—R$^1$—" (i.e. R$^1$ is absent in only one of the two compounds making up the dimeric substance); or "R$^1$—B—R" in Formula IV represents a single bond bridge ("—", i.e. R, B and R$^1$ are absent), or a bridging group of the formula "R$^1$—R—" (i.e. B is absent); or "R$^1$—B" in Formula IV represents a single bond bridge ("—", i.e. R$^1$ and B are absent, R is present); or R and/or R$^1$, together with the nitrogen atom to which they are attached represent an alkyl-onium salt, a dialkyl-onium salt, a cycloalkyl-onium salt, an alkyl-cycloalkyl-onium salt, a dicycloalkyl-onium salt, an alkyl-cycloalkyla-lkyl-onium salt, a cycloalkyl-cycloalkylalkyl-onium salt, or a dicycloalkylalkyl-onium salt; and B represent a singl bond bridge ("—", i.e. B is absent), or a bridging element of the formula "—ALK—", "—ALK—X—ALK—", "—X—ALK—X—", "—PHE—", "—X—PHE—X", or "—ALK—PHE—ALK—"; wherein "ALK" represents a single bond bridge ("—", i.e. ALK is absent) or alkyl, alkenyl, or alkynyl; and "PHE" represents a phenylene (benzene-diyl) group; and X represents O, S, NH, N-alkyl or Se.

In another aspect of the invention provides pharmaceutical compositions comprising a therapeutically-effective amount of a diazacycloalkane derivative of the invention, or pharmaceutically-acceptable addition salts thereof, together with at least one pharmaceutically-acceptable carrier or diluent.

In a third aspect the invention relates to the use of the diazacycloalkane derivatives of the invention for the manufacture of a pharmaceutical composition for the diagnosis, treatment, prevention or alleviation of a disease or a disorder or a condition of a mammal, including a human, which disease, disorder or condtion is responsive to the activity of nAChR modulators.

In a fourth aspect the invention provides a method for diagnosis, treatment, prevention or alleviation of a disease or a disorder or a condition of a living animal body, including a human, which disorder, disease or condition is responsive to the activity of nAChR modulators, comprising the step of administering to such a living animal body, including a human, in need thereof a therapeutically effective amount of a diazacycloalkane derivative of the invention.

Other objects of the invention will be apparent to the person skilled in the art from the following detailed description and examples.

DETAILED DISCLOSURE OF THE INVENTION

Diazacycloalkane Derivatives

In a first aspect novel diazacycloalkane derivatives are provided. The diazocycloalkane derivatives of the invention may be represented by the general Formula I

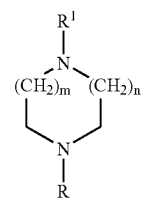

or they may be dimeric compounds thereof represented by any of the Formulae II, III or IV

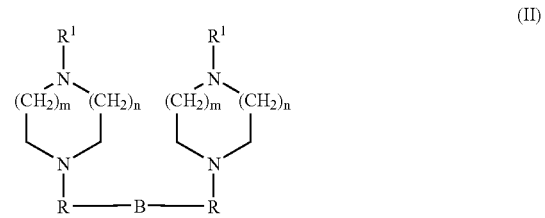

(II)

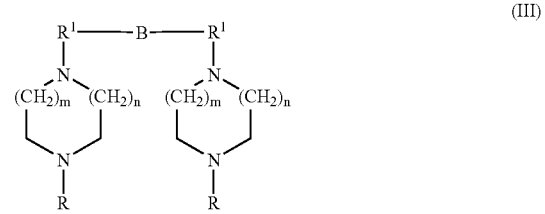

(III)

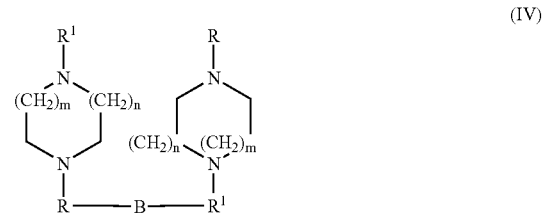

(IV)

in which formulae, n is 1, 2 or 3; and m is 0, 1 or 2; and

R represents hydrogen, an alkyl group, a cycloalkyl group, a cycloalkylalkyl group, an alkenyl group, an alkynyl group, an aralkyl group, an alkoxypyridyl group, or an alkenoxypyridyl group; or "—R—B—R—" in Formula II represents a single bond bridge ("—", i.e. R and B are absent), or a bridging group of the formula "R—R—" (i.e. B is absent), or a bridging group of the formula "—R—" (i.e. R is absent in only one of the two compounds making up the dimeric substance); or "R—B—R$^1$" in Formula IV represents a single bond bridge ("—", i.e. R, B and R$^1$ are absent), or a bridging group of the formula "R—R$^1$—" (i.e. B is absent); or "R—B" in Formula IV represents a single bond bridge ("—", i.e. R and B are absent, R$^1$ is present); or R and R$^1$ are identical and represent a monocyclic 5 to 6 membered heterocyclic group which heterocyclic group may be substituted one or more times with alkyl, alkoxy, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, —NH—CO$_2$R$^2$, —NHCO—R$^2$ or —OCO—NR$^2$R$^3$, in which formulae R$^2$ and R$^3$ independently of each another represents hydrogen or alkyl; and R$^1$ represents a monocyclic 5 to 6 membered heterocyclic group, which heterocyclic group may be substituted one or more times with alkyl, alkoxy, cycloalkyl, cycloalkoxy, alkoxycycloalkyl, cycloalkoxyalkyoxy, cycloalkylalkyl, ydroxyalkoxy, alkenyl, alkoxyalkenyl, alkynyl, alkoxyalkynyl, alkenoxy, alkynoxy, lkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, —NH—CO$_2$R$^2$, —NHCO—R$^2$ or —OCO—NR$^2$R$^3$; in which formulae R$^2$ and R$^3$ independently of each another represents hydrogen or alkyl; or which heterocyclic group may be substituted with an aryl group, which aryl group may optionally be substituted one or more times with alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which heterocyclic group may be substituted with a group of the formula "—X-alkyl-Y-alkyl", in which formual X and Y independently of each another represent O (epoxy), S, NH, N-alkyl or Se; and alkyl is optionally substituted with alkoxy, or alkylthio; or which heterocyclic group may be substituted with a group of the formula "—X—(ALK)$_o$-aryl", in which formula X represents O, S, NH, N-alkyl or Se; "ALK" represents alkyl, alkenyl or alkynyl; aryl is optionally substituted one or more times with alkyl, cycloalkyl, cycloalkylalkyl alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; and o is 0 or 1; or which heterocyclic group may be substituted with a group of the formula "—X—(ALK)$_o$—Z", in which formula "ALK" represents alkyl, alkenyl or alkynyl; X represents O, S, NH, N-alkyl or Se; Z represents a 5- or 6-membered monocylic heterocyclic group, which heterocyclic group is optionally substituted one or more times with alkyl, cycloalkyl, cycloalkylalkyl alkeny, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; and o is 0 or 1; or Which heterocyclic group may be substituted with another monocyclic 5 to 6 membered heterocyclic group, which additional heterocyclic group may be substituted one or more times with alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which heterocyclic group may be substituted with a group of the formula "(ALK)$_o$-HET", in which formula "ALK" represents alkyl, alkenyl, or alkynyl; o is 0 or 1; and HET represents a non-aromatic heterocyclic group; or or R$^1$ represents a bicyclic heterocyclic group, which bicyclic group is composed of a 5 to 6 membered monocyclic heterocyclic group fused to a benzene ring, which bicyclic group may be substituted one or more times with alkyl, alkoxy, alkoxy-alkoxy, cycloalkyl, cycloalkoxy, alkoxycycloalkyl, cycloalkoxyalkoxy, cycloalkylalkyl, hydroxyalkoxy, alkenyl, alkoxyalkenyl, alkynyl, alkoxyalkynyl, alkenoxy, alkynoxy, alkylthio, alkenylthio, alkynylthio, alkylseleno, alkenylseleno, alkynylseleno, methylenedioxy, trifluoromethanesulfonyloxy, halogen, —OH, —CF$_3$, —OCF$_3$, —CN, amino, nitro, oxime, alkyloxime, acyloxime, or a group of the formula —COOR$^3$, —CONR$^2$R$^3$, each another represents hydrogen or alkyl; or which bicyclic group may be substituted with an aryl gorup, which aryl group is optionally substituted one or more times with alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or which bicyclic group may be substituted with an additional monocyclic 5 to 6 membered heterocyclic group, which additional heterocyclic group is optionally substituted one or more times wiht alkyl, cycloalkyl, cycloalkylalkyl, alkenyl, alkynyl, alkoxy, cycloalkoxy, alkenoxy, alkynoxy, methylenedioxy, halogen, —OH, —CF$_3$, —OCF$_3$, —CN, amino, nitro, oxime, alkyloxime, acyloxime; or "R$^1$—B—R$^1$—" in Formula III represents a single bond bridge ("—", i.e. R$^1$ and B are absent), or a bridging group of the formula "R$^1$—R$^1$—" (i.e. B is absent), or a bridging group of the formula "—R$^1$—" (i.e. R$^1$ is absentin only one of the two compounds making up the dimeric substance); or "R$^1$—B—R" in Formula IV represents a single bond bridge ("—", i.e. R, B and R$^1$ are absent), or a bridging group of the formula "R$^1$—R—" (i.e. B is absent); or "R$^1$—B" in Formula IV represents a single bond bridge ("—", i.e. R$^1$ and B are absent, R is present); or R and/or R$^1$, together with the nitrogen atom to which they are attached, represent an alkyl-onium salt, a dialkyl-onium salt, a cycloalkyl-onium salt, an alkyl-cycloalkyl-onium salt, a dicycloalkyl-onium salt, an alkyl-cycloalkylalkyl-onium salt, a cycloalkyl-cycloalkylalkyl-onium salt, or a dicycloalkylalkyl-onium salt; and B represents a single bond bridge ("—", i.e. B is absent), or a bridging element of the formula "—ALK—", "—ALK—X—ALK—", "X—ALK—X—", "—PHE—", "—X—PHE—X—", or "—ALK—PHE—ALK—", wherein "ALK" represents a single bond bridge ("—", i.e. ALK is absent), or alkyl, alkenyl, or alkynyl; and "PHE" represents a phenylene (benzene-diyl) group; and X represents O, S, NH, N-alkyl or Se.

Moreover, the diazacycloalkane derivatives of the invention may be an enantiomers or a mixture of enantiomers (isomers), an N oxide, a pharmaceutically acceptable salt, of a compound of any of Formulae I, II, III or IV. Moreover, the compound may be provided in labelled or un-labelled form.

In a preferred embodiment the diazacycloalkane group is imidazolidine, pyridine, 1,3-diazacyclohexane, piperazine, homopiperazine, 1,4-azacyclooctane, or 1,5-azacyclooctane.

In another preferred embodiment R$^1$ represents an optionally substituted heteroaryl.

In a more preferred embodiment R$^1$ represents pyridinyl, pyridazinyl, quinolinyl or isoquinolinyl, which heteroaryl group is optionally substituted one or more times with alkyl, alkoxy, cycloalkoxy, alkoxyalkoxy, alkoxyalkenyl, alkoxyalkynyl, alkynyl, alkenyl, alkenylthio, alkylseleno, alkoxycycloalkyl, hydroxyalkoxy, alkylthio, arylalkylthio, alkenoxy, alkynoxy, carboxylamido, arylalkylthio, arylthio, hydroxy, trifluoromethanesfulfonyloxy, halogen; phenyl; phenyl substituted with alkyl, alkoxy, hydroxy, amino, or nitro; a monocyclic 5 to 6 membered heterocyclic group; a monocyclic 5 to 6 membered heterocyclic group substituted with alkyl, alkoxy, hydroxy, amino or nitro; a bicyclic heterocyclic group; or a bicyclic heterocyclic group substituted with alkyl, alkoxy, hydroxy, amino or nitro.

In a yet more preferred embodiment $R^1$ represents 5-(1-heptynyl)-3-pyridyl; 5-(1-hexynyl)-3-pyridyl; 5-(1-pentynl)-3-pyridyl; 5-(1-butynyl)-3-pyridyl; 5-(1-propynyl)-3-pyridyl; 5-ethylenethio-3-pyridyl; 5-(1-propylenethio)-3-pyridyl; 5-(1-butylenethio)-3- pyridyl; 5-(1-pentylenethio)-3pyridyl; 5-ethyleneseleno-3-pyridyl; 5-(1-propyleneseleno)-3-pyridyl; 5-(1-butyleneseleno)-3-pyridyl; 5-(1-pentyleneseleno)-3- pyridyl; 5-methylseleno-3-pyridyl; 5-ethylseleno-3-pyridyl; 5-propylseleno-3-pyridyl; 5-butylseleno-3-pyridyl; 1-[5-1-butyl-N-methylamino)3-pyridyl]; 5-(N-azacylobutenyl)-3- pyridyl; 5-(N-2-pyrrolinyl)-3-pyridinyl; 5-(N-3-pyrrolinyl)-3-pyridinyl; 5-N-(1,4,5,6-tetrahydropyridinyl)-3-pyridyl; 5-N-(1,2,5,6-tetrahydropyridinyl)-3-pyridyl; 5-(homopiperazinyl)-3-pyridyl; 5,6-dibromo-3-pyridyl; 5-bromo-6-chloro-3-pyridyl; 6-bromo-5-chloro-3-pyridyl; 6-bromo-3-pyridyl; 5,6-dichloro-3-pyridyl; 6-fluoro-3-pyridyl; 6-iodo-3-pyridyl; 5-chloro-6-fluoro-3-pyridyl; 5-chloro-6-iodo-3-pyridyl; 5-bromo-6-fluoro-3-pyridyl; 5-bromo-6-iodo-3-pyridyl; 6-fluoro-pyridazinyl; 6-iodopyridazinyl; 5-pentyloxy-3-pyridyl; 5-(trans-hex-2-en-1-yl-oxy)-3-pyridyl; 5-butoxy-3-pyridyl; 5-methoxy-3-pyridyl; 5-propyloxy-3-pyridyl; 5-homoperazinyl-3-pyridyl; 5-ethoxy-3- pyridyl; 5-propyl-1,2-epoxy-1-oxy-3-pyridyl; 5-phenylacetylenyl-3-pyridyl; 5-(2-ethyl-1- butoxy)-3-pyridyl; 5-(1-methyl-1-prop-2-en-oxy)-3-pyridyl; 5-(cyclobutylmethoxy)-3- pyridyl; 5-(hex-2-en-oxy)-3-pyridyl; 5-(2-methyl-1-prop-1-en-oxy)-3-pyridyl; 5-(1- piperidinyl)-3-pyridyl; 5-(N-azacycloheptyl)-3-pyridyl; 5-(N-azacyclooctanyl)-3-pyridyl; or 5-(1-morpholinyl)-3-pyridyl.

In a most preferred embodiment the diazacycloalkane derivative of the invention is 5-(1-heptynyl)-3-pyridyl-homopiperzaine; 5-(1-hexynyl)-3-pyridyl- homopiperazine; 5-(1-pentynyl)-3-pyridyl-homopiperazine; 5-(1-butynyl)-3-pyridyl- homopiperazine; 5-(1-propynyl)-3-pyridyl-homopiperazine; 5-ethylenethio-3-pyridyl- homopiperazine; 5-(1-propylenethio)-3-pyridyl-homopiperazine; 5-(1-butylenethio)-3- pyridyl-homopiperazine; 5-(1-pentylenethio)-3-pyridyl-homopiperazine; 5-ethyleneseleno-3-pyridyl-homopiperazine; 5-(1-propyleneseleno)-3-pyridyl-homopiperazine; 5-(1-butyleneseleno)-3-pyridyl-homopiperazine; 5-(1-pentyleneseleno)-3-pyridyl-homopiperazine; 5-methylseleno-3-pyridyl- homopiperazine; 5-ethylseleno-3-pyridyl-homopiperazine; 5-propylseleno-3-pyridyl-homopiperazone; 5-butylseleno-3-pyridyl-homopiperazine; 5-(1-azacyclobutene)-3- pyridyl-homopiperazine; 5-(dihydro-pyrrole)-3-pyridyl-homopiperazine; 5-(tetrahydropyridine)-3-pyridyl-homopiperazine; 5-(homopiperazine)-3-pyridyl- homopiperazine; 5,6-dichloro-3-pyridyl-homopiperazine; 6-fluoro-3-pyridyl- homopiperazine; 6-iodo-3-pyridyl-homopiperazine; 5-chloro-6-fluoro-3-pyridyl- homopiperazine; 5-chloro-6-iodo-3-pyridyl-homopiperazine; 5-bromo-6-fluoro-3- pyridyl-homopiperazine; 5-bromo-6-iodo-3-pyridyl-homopiperazine; 6-fluoro-pyridazine-homopiperazine; 6-iodopyridazine-homopiperazine; 5-pentyloxy-3-pyridyl- homopiperazine; 5-pentyloxy-3-pyridyl-piperazine; 5-(trans-hex-2-en-1-yl-oxy)-3-pyridyl-homopiperazine; 5-(trans-hex-2-en-1-yl-oxy)-3-pyridyl-piperazine; 5-butoxy-3- pyridyl-1,5-diazacyclooctane; 5-methoxy-3-pyridyl-4-ethyl-piperazine; 4-methyl-1-(5-propyloxy-3-pyridyl)-piperazine; 3,5-Bis-(N,N'-homopiperazinyl)-pyridine; 5-ethoxy-3- pyridyl-4-ethyl-homopiperazine; 5-ethoxy-3-pyridyl-4-propyl-homopiperazine; 5-ethoxy- 3-pyridyl-4-(prop-2-en-1-yl)-homopiperazine; 5-propyl-1,2-epoxy-1-oxy-3-pyridyl- homopiperazine; 5-phenylacetylenyl-3-pyridyl-homopiperazine; 1-(5-(2-ethyl-1- butoxy)-3-pyridyl)-homopiperazine; 1-(5-(1-methyl-1-prop-2-en-oxy)-3-pyridyl)- homopiperazine; 1-(5-cyclobutylmethoxy)-3-pyridyl)-homopiperazine; 1-(5-(hex-2-en- oxy)-3-pyridyl)-homopiperazine; 1-(5-(2-methyl-1-prop-1-en-oxy)-3-pyridyl)- homopiperazine; 1,4-Bis-[5-ethoxy-3-pyridyl]-homopiperazine; 1,4-Bis-[5-(1-propyl-1-en-oxy)-3-pyridyl]-homopiperazine; 1-(5-Iodo-3-pyridyl)-homopiperazine; 1-[5-(N- Azetidinyl)-3-pyridyl]-homopiperazine; 1,4-Bis-[5-(vinyl-oxy)-3-pyridyl]- homopiperazine; 1-[5-Phenyl-2-eth-1-yl-3-pyridyl]-homopiperazine; 1-[5-Ethyl-3- pyridyl]-homopiperzine; 1-[3-(4-Chloro-1,2,5-thiadiazolyl)]-homopiperazine; 1-(5- Chloro-3-pyridyl)-homopiperazine; 1-(5-Bromo-3-pyridyl)-homopiperazine; 1-[5- Chloro-3-pyridyl]-1,5-diazacyclooctane; 1-[5-Bromo-3-pyridyl]-1,5-diazacylooctane, 1-(3-Pyridyl)-1,5-diazacyclooctane; 1-(6-Amino-3-pyridyl)-homopiperazine; 1-(6-Nitro- 3-pyridyl)-homopiperazine; 1-[3-(1,2,5-thiadiazolyl)]-homopiperazine; 1-[3-(1,3,4- thiadiazolyl)]-homopiperazine; 1-(6-Fluoro-5-ethynyl-3-pyridyl)-homopiperazine; 1-(6- Chloro-5-ethynyl-3-pyridyl)-homopiperazine; 1-(6-Bromo-5-ethynyl-3-pyridyl)-homopiperazine; 1-(6-Iodo-5-ethynyl-3-pyridyl)-homopiperazine; 1-(6-Fluoro-5-propyn- 1-yl-3-pyridyl)-homopiperazine; 1-(6-Chloro-5-propyn-1-yl-3-pyridyl)-homopiperazine; 1-(6-Bromo-5-propyn-1-yl-3-pyridyl)-homopiperazine; 1-(6-Iodo-5-propyn-1-yl-3- pyridyl)-homopiperazine; 1-(6-Fluoro-5-butyn-1-yl-3-pyridyl)-homopiperazine; 1-(6- Chloro-5-butyn-1-yl-3-pyridyl)-homopiperazine; 1-(6-Bromo-5-butyn-1-yl-3-pyridyl)-homopiperazine; 1-(6-Iodo-5-butyn-1-yl-3-pyridyl)-homopiperazine; 1-(6-Fluoro-5- pentyn-1-yl-3-pyridyl)-homopiperazine; 1-(6-Chloro-5-pentyn-1-yl-3-pyridyl)-homopiperazine; 1-(6-Bromo-5-pentyn-1-yl-3-pyridyl)-homopiperazine; 1-(6-Iodo-5- pentyn-1-yl-3-pyridyl)-homopiperazine; 1-(6-Fluoro-5-ethenyl-3-pyridyl)- homopiperazine; 1-(6-Chloro-5-ethenyl-3-pyridyl)-homopiperazine; 1-(6-Bromo-5- ethenyl-3-pyridyl)-homopiperazine; 1-(6-Iodo-5-ethenyl-3-pyridyl)-homopiperzine; 1- (6-Fluoro-5-propen-1-yl-3-pyridyl)-homopiperazine; 1-(6-Chloro-5-propen-1-yl-3- pyridyl)-homopiperazine; 1-(6-Bromo-5-propen-1-yl-3-pyridyl)-homopiperazine; 1-(6- Iodo-5-propen-1-yl-3-pyridyl)-homopiperazine; 1-(6-Fluoro-5-buten-1-yl-3-pyridyl)- homopiperazine; 1-(6-Chloro-5-buten-1-yl-3pyridyl)-homopiperazine; 1-(6-Bromo-5- butyn-1-yl-3-pyridyl)-homopiperazine; 1-(6-Iodo-5-buten-1-yl-3-pyridyl)- homopiperazine; 1-(6-Fluoro-5-penten-1-yl-3-pyridyl)-homopiperazine; 1-(6-Chloro-5- penten-1-yl-3-pyridyl)-homopiperazine; 1-(6-Bromo-5-penten-1-yl-3-pyridyl)- homopiperazine; 1-(6-Iodo-5-penten-1-yl-3-pyridyl)-homopiperazine; 1-(6-Fluoro-5- ethyl-3-pyridyl)-homopiperazine; 1-(6-Chloro-5-ethyl)-3-pyridyl)-homopiperazine; 1-(6- Bromo-5-ethyl-3-pyridyl)-homopiperazine; 1-(6-Iodo-5-ethyl-3-pyridyl)-homopiperazine; 1-(6-Fluoro-5-prop-1-yl-3-pyridyl)-homopiperazine; 1-(6-Chloro-5- prop-1-yl-3-pyridyl)-homopiperazine; 1-(6-Bromo-5-prop-1-yl-3-pyridyl)- homopiperazine; 1-(6-Iodo-5-prop-1-yl-3-pyridyl)-homopiperazine; 1-(6-Fluoro-5-but-1- yl-3-pyridyl)-homopiperazine; 1-(6-Chloro-5-but-1-yl-3-pyridyl)-homopiperazine; 1-(6- Bromo-5-but-1-yl-3-pyridyl)-homopiperazine; 1-(6-

Iodo-5-but-1-yl-3-pyridyl)- homopiperazine; 1-(6-Fluoro-5-pent-1-yl-3-pyridyl)-homopiperazine; 1-(6-Chloro-5- pent-1-yl-3-pyridyl)-homopiperazine; 1-(6-Bromo-5-pent-1-yl-3-pyridyl)- homopiperazine; 1-(6-Iodo-5-pent-1-yl-3-pyridyl)-homopiperazine; 1-(6-Bromo-5- methoxy-3-pyridyl)-homopiperazine; 1-(6-Chloro-5-methoxy-3-pyridyl)- homopiperazine; 1-(6-Fluoro-5-methoxy-3-pyridyl)-homopiperazine; 1-(6-Iodo-5- methoxy-3-pyridyl)-homopiperazine; 1-(6-Chloro-5-ethoxy-3-pyridyl)-homopiperazine; 1-(6-Fluoro-5-ethoxy-3-pyridyl)-homopiperazine; 1-(6-Iodo-5-ethoxy-3-pyridyl)-homopiperazine; 1-(6-Bromo-5-propyloxy-3-pyridyl)-homopiperazine; 1-(6-Chloro-5- propyloxy-3-pyridyl)-homopiperazine; 1-(6-Fluoro-5-propyloxy-3-pyridyl)-homopiperazine; 1-(6-Iodo-5-propyloxy-3-pyridyl)-homopiperazine; 1-(6-Bromo-5- vinyloxy-3-pyridyl)-homopiperazine; 1-(6-Chloro-5-vinyloxy-3-pyridyl)-homopiperazine; 1-(6-Fluoro-5-vinyloxy-3-pyridyl)-homopiperazine; 1-(6-Iodo-5-vinyloxy-3-pyridyl)-homopiperazine; 1-(3-Pyridyl)-1,5-diazacyclooctane; 1-(6-Nitro-3-pyridyl)- homopiperazine; 1-(6-Amino-3-pyridyl)-homopiperazine; 1-(6-Fluoro-5-ethynyl-3- pyridyl)-homopiperazine; 1-(6-Chloro-5-ethynyl-3-pyridyl)-homopiperzine; 1-(6- Bromo-5-ethynyl-3-pyridyl)-homopiperazine; 1-(6-Iodo-5-ethynyl-3-pyridyl)-homopiperazine; 1-(6-Fluoro-5-propyn-1-yl-3-pyridyl)-homopiperazine; 1-(6-Chloro-5- propyn-1-yl-3-pryidyl)-homopiperazine; 1-(6-Bromo-5-propyn-1-yl-3-pyridyl)-homopiperazine; 1-(6-Iodo-5-propyn-1-yl-3-pyridyl)-homopiperazine; 1-(6-Fluoro-5- butyn-1-yl-3-pyridyl)-homopiperazine; 1-(6-Chloro-5-butyn-1-yl-3-pyridyl)-homopiperzine; 1-(6-Bromo-5-butyn-1-yl-3-pyridyl)-homopiperazine; 1-(6-Iodo-5- butyn-1-yl-3-pyridyl)-homopiperazine; 1-(6-Fluoro-5-pentyn-1-yl-3-pyridyl)- homopiperazine; 1-(6-Chloro-5-pentyn-1-yl-3-pyridyl)-homopiperazine; 1-(6-Bromo-5- pentyn-1-yl-3-pyridyl)-homopiperazine; 1-(6-Iodo-5-pentyn-1-yl-3-pyridyl)-homopiperazine; 1-(5-Ethenyl-3-pyridyl)-homopiperazine; 1-(5-Propen-1-yl-3pyridyl)- homopiperazine; 1-(5-buten-1-yl-3-pyridyl)-homopiperazine; 1-(5-Penten-1-yl-3- pyridyl)-homopiperazine; 1-(5-Prop-1-yl-3-pyridyl)-homopiperzine; 1-(5-But-1-yl-3- pyridyl)-homopiperazine; or 1-(5-Pent-1-yl-3-pyridyl)-homopiperazine;

any of its enantiomers or any mixture thereof, an N oxide thereof, a pharmaceutically acceptable salt thereof, in a labelled or un-labelled form.

In another preferred embodiment the diazacycloalkane derivative of the invention is a compound of Formula III, wherein "—R¹—B—R¹—" represents a single bond bridge ("—", i.e. R¹ and B are absent), or a bridging group of the formula "R¹—R¹—" (i.e. B is absent), or a bridging group of the formula "—R¹—" (i.e. R¹ is absent in only one of the two compounds making up the dimeric substance); or B is bridging group of the formula "—X—ALK—X—", wherein "ALK" represents $C_{1-4}$-alkyl; or B is a bridging group of the formula "—ALK—PHE—ALK—", wherein "ALK" represents $C_{1-4}$-alkyl, and "PHE" represents a phenylene group.

In a more preferred embodiment the diazacycloalkane derivative of the invention is 3,5-Bis-(N,N'-homopiperazine)-pyridine; 1,4-[α,α'-Bis-(5-Ethoxy-3-pyridyl- 1-homopiperazinyl)]-dimethylbenzene; 1,4-[α,α'-Bis-(6-Chloro-3-pyridazinyl-1- homopiperazinyl)]-dimethylbenzene; O,O'-Bis-[5-(1-homopiperazinyl)-3-pyridyl]- ethyleneglycol; or Homopiperazinyl-5-pyrid-3-yl-homopiperazine; any of its enantiomers or any mixture thereof, an N oxide thereof, a pharmaceutically acceptable salt thereof, in a labelled or un-labelled form.

Definition of Substituents

In the context of this invention halogen represents fluorine, chlorine, bromine or iodine.

In the context of this invention an alkyl group designates a univalent saturated, straight or branched hydrocarbon chain. The hydrocarbon chain preferably contain of from one to eighteen carbon atoms ($C_{1-6}$-alkyl), more preferred of from one to eight carbon atoms ($C_{1-8}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl, or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3- butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbin chain containing one or more triple bonds, including di-ynes, tri-ynes, and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, 3-butynyl, or 1,3- butynyl; 1-, 2-, 3-, 4-pentynyl, or 1,3-pentynyl; 1-, 2-, 3-, 4-, or 5-henynyl, or 1,3- hexynyl or 1,3,5-hexynyl; 1-, 2-, 3-, 4-, 5- or 6-heptynyl, or 1,3-heptynyl, or 1,3,5- heptynyl; 1-, 2-, 3-, 4-, 5-, 6- or 7-octynyl, or 1,3-octynyl, or 1,3,5-octynyl, or 1,3,5,7-octynyl.

In the context of this invention a monocyclic heterocyclic group is a monocyclic compound, which holds one or more heteroatoms in its ring structure. Preferred heteroatoms include nitrogen (N), oxygen (O), and sulphur (S). The ring structure may in particular be aromatic (i.e. a heteroaryl), or saturated or partially saturated ("HET"). Preferred heterocyclic monocyclic groups of the invention include 5- and 6 membered heterocyclic monocyclic groups.

Examples of preferred aromatic heterocyclic 5-membered monocyclic groups of the invention include furan, in particular 2- or 3-furanyl;
thiophene, in particular 2- or 3-thienyl;
pyrrole, in particular 1-, 2- or 3-pyrrolyl;
oxazole, in particular oxazol-(2-,4- or 5-)-yl;
thiazole, in particular thiazol-(2-,4-, or 5-)-yl;
imidazole, in particular imidazol-(1-,2-,4- or 5-)yl;
pyrazole, in particular pyrazol-(1-,3-, 4- or 5-)yl;
isoxazole, in particular isoxazol-(3-,4- or 5-)yl;
isothiazole, in particular isothiazol-(3-,4- or 5-)yl;
1,2,3-oxadiazole, in particular 1,2,3-oxadiazol-(4- or 5-)yl;
1,2,4-oxadiazole, in particular 1,2,4-oxadiazol-(3- or 5-)yl;
1,2,5-oxadiazole, in particular 1,2,5-oxadiazol-(3- or 4-)yl;
1,2,3-triazole, in particular 1,2,3-triazol-(1-,4- or 5-)yl;

1,2,4-thiadiazole, in particular 1,2,4-thiadiazol-(3- or 5-)yl;
1,2,5-thiadiazole, in particular 1,2,5-thiadiazol-(3- or 4-)yl;
1,3,4-thiadiazole, in particular 1,3,4-thiadiazol-(2- or 5-)yl;

Examples of preferred aromatic heterocyclic 6-membered monocyclic groups of the invention include
pyridine, in particular pyridin-(2-, 3- or 4-)yl;
pyriadaine, in particular pyridazin-(3- or 4-)yl;
pyrimidine, in particular pyrimidin-(2-,4- or 5-)yl;
pyrazine, in particular pyrazin-(2-, or 3-)yl;
1,3,5-triazine, in particular 1,3,5-triazin-(2-,4- or 6-)yl; and
phosphinine, in particular phosphinin-(2-,3- or 4-)yl;

In the context of this invention a bicyclic heterocyclic group is a bicyclic compound composed of a monocylic 5 to 6 membered heterocyclic group as described above, which heterocyclic group is fused to a benzene ring.

Examples of preferred aromatic heterocyclic bi-cyclic groups of the invention include
indolizine, in particular indolizin-(1-,2-,3-,5-,6-,7- or 8)yl;
indole, in particular indol-(1-,2-,3-,4-,5-,6- or 7)yl;
isoindole, in particular isoindol-(1-,2-,3-,4-,5-,6- or 7-)yl;
benzo[b]furan (benzofuran), in particular benzo[b]furan-(2-,3-,4-,5-,6- or 7-)yl;
benzo[b]furan (benzofuran), in particular benzo[b]furan-(2-,3-,4-,5-,6- or 7-)yl;
benzo[b]furan (isobenzofuran), in particular benzo[c]furan-(1,3-,4-,5-,6- or 7-)yl;
benzo[b]thiophene (benzothiophene), in particular benzo[b]thiophen-(2-,3-,4-,5-, 6- or 7-)yl;
benzo[c]thiophene (isobenzothiophene), in particular benzo[c]thiophen-(1-,3-,4-, 5-,6- or 7-)yl;
benzimidazole, in particular benzimidazol-(1,2-,4-,5-,6- or 7-)yl;
benzthiazole, in particular benzthiazol-(2-,4-,5-,6- or 7-)yl;
purine, in particular purin-(2-,6- or 8-)yl;
quinoline, in particular quinolin-(2-,3-,4-,5-,6-,7- or 8-)yl;
isoquinoline, in particular isoquinolin-(1-,3-,4-,5-6-,7- or 8-)yl;
cinnoline, in particular cinnolin-(3-,4-,5-,6-7- or 8-)yl;
phthlazine, in particular phthlazin-(1-,4-,5-,6-,7- or 8-)yl;
quinazoline, in particular quinazolin-(2-,4-,5-,6-,7- or 8-)yl;
quinoxaline, in particular quinoxalin-(2-,3-,5-,6-,7- or 8-)yl;
1,8-naphthyridine, in particular 1,8-naphthyridin-(2-,3-,4-,5-,6- or 7-)yl; and
pteridine, in particular pteridin-(2-,4-,6- or 7-)yl;

Examples of preferred saturated or partially saturated heterocyclic bi-cyclic groups of the invention include
indoline, in particular indolin-(1-,2-,3-,4-,5-,6- or 7-)yl;
3H-indole, in particular 3H-indol-(2-,3-,4-,5-,6- or 7-)yl;
1H-indazole, in particular 1H-indazol-(3-,4-,5-,6- or 7-)yl;
4H-quinolizine, in particular 4H-quinolizin-(1-,2-,3-,4-6-,7-,8- or 9-)yl;
quinuclidine, in particular quinuclidin-(2-,3-,4-,5-,6-,7- or 8-)yl;
isoquinuclidine, in particular isoquinuclidin-(1-,2-,3-,4-,5-,6-,7- or 8-)yl;
tropane, in particular tropan-(1-,2-,3-,4-,5-,6-,7- or 8-)yl; and
nortropane, in particular nortropan-(1-,2-,3-,4-,5-,6-, or 7-)yl;

In the context of this invention "HET" represents a non-aromatic (i.e. saturated or partially saturated) monocyclic heterocyclic group containing at least one heteroatom.

Examples of preferred non-aromatic heterocyclic monocyclic 3- or 4- membered groups of the invention include aziridine; azetidine; and azacyclobutene;

Examples of preferred non-aromatic heterocyclic monocyclic 5-membered groups of the invention include
2H-pyrrole, in particular 2H-pyrrol-(2- or 3-)yl;
3H-pyrrole, in particular 3H-pyrrol-(2- or 3-)yl;
2,3-dihydro-pyrrole, in particular 2,3-dihydro-pyrrol-(2- or 3-)yl;
3,4-dihydro-pyrrole, in particular 3,4-dihydro-pyrrol-(2- or 3-)yl;
2-pyrroline, in particular 2-pyrrolin-(1-,2- or 3-)yl;
3-pyrroline, in particular 3-pyrrolin(1-,2- or 3-)yl;
pyrrolidine, in particular pyrrolidin-(1-,2- or 3-)yl;
1,3-dioxolan, in particular 1,3-dioxolan-(2- or 4-)yl;
imidazolidine, in particular imidazolidin-(1-,2-,3-,4- or 5-)yl;
2-imidazoline, in particular 2-imidazolin-(1-,2-,4- or 5-)yl;
3-imidazoline, in particular 3-imidazolin-(1-,2-,4- or 5-)yl;
4-imidazoline, in particular 4-imidazolin-(1-,2-,4- or 5-)yl;
pyrazolidine, in particular pyrazolidin-(1-,2-,3-,4- or 5-)yl;
2-pyrazoline, in particular 2-pyrazolin-(1-,3-,4- or 5-)yl; and 3-pyrazoline, in particular 3-pyrazolin-(1-,3-,4- or 5-)yl;

Examples of preferred non-aromatic heterocyclic monocyclic 6-membered groups of the invention include
2,3-dihydropyridine, in particular 2,3-dihydropyridin-(2-, 3- or 4-)yl;
3,4-dihydropyridine, in particular 3,4-dihydropyridin-(2-, 3- or 4-)yl;
4,5-dihydropyridine, in particular 4,5-dihydropyridin-(2-, 3- or 4-)yl;
5,6-dihydropyridine, in particular 5,6-dihydropyridin-(2-, 3- or 4-)yl;
2H-pyrane, in particular 2H-pyran-(2-,3- or 4-)yl;
4H-pyrane, in particular 4H-pyran-(2-,3- or 4-)yl;
piperidine, in particular piperidin-(1-,2-,3- or 4-)yl;
1,4-dioxolane, in particular 1,4-dioxolan-(2- or 3-)yl;
morpholine, in particular morpholin-(2-,3- or 4-)yl;
1,4-dithiane, in particular 1,4-dithian-(2- or 3-)yl;
thiomorpholine, in particular thiomorpholin-(2-,3- or 4-)yl;
piperazine, in particular piperazin-(1-,2-,3- or 4-)yl;
1,3,5-trithiane, in particular 1,3,5-trithian-(2-)yl; and
1,4-oxazine, in particular 1,4-oxazin-(2-)yl; and
morpholine, in particular morpholin-(2- or 3-)yl;

Examples of preferred non-aromatic heterocyclic monocyclic 7- to 8-membered groups of the invention include homopiperidine; homopiperazine; azacyclooctane; and diazacyclooctane.

Pharmaceutically Acceptable Salts

The chemical compound of the invention may be provided in any form suitable for the intended administration. Suitable forms include pharmceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzenesulphonic acid, the benzoate derived from benozic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N- and/or S-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indossoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indossoluble forms for the purpose of this invention.

Labelled Compounds

The compounds of the invention may be used in their labelled or unlabelled form. In the context of this invention "label" stands for the binding of a marker to the compound of interest that will allow easy quantitative detection of said compound.

The compounds of the invention may be useful as diagnostic tools, radio tracers, or monitoring agents in various diagnostic methods, and in particular for in vivo receptor imaging, where they are preferably employed in labelled form.

In the context of this invention an isotopes designates a labelled compound in which one or more atoms has been changed into an isotope of the naturally occurring atom. Labelled compounds and includes though not limited to $^2$H (deuterium), $^3$H (tritium), $^{13}$C, $^{14}$C, $^{131}$I, $^{125}$I, $^{123}$I, $^{18}$F, as described in more details below (under "neuroimaging").

Steric Isomers

It will be appreciated by those skilled in the art that the compounds of the present invention may contain one or more chiral centres, and that such compounds exist in the form of isomers (i.e. enantiomers). The invention includes all such isomers and any mixtures thereof including racemic mixtures.

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those describe by Jaques J, Collet A, & Wilen S in "*Enantiomers, Racemates, and Resolutions*", John Wiley Sons, New York (1981).

Optical active compounds can also be prepared from optical active staring materials.

Moreover, some of the chemical compounds of the invention being oximes, may thus exist in two forms, syn- and anti-form (Z- and E-form), depending on the arrangement of the sbustituents around the —C=N— double bond. A chemical compound of the present invention may thus be the syn- or the anti-form (Z- and E- form), or it may be a mixture hereof.

Methods of Producing Diazacycloalkane Derivatives

The diazacycloalkane derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The diazacycloalkane derivatives of the present invention are nicotinic receptor modulators. In the context of this invention the term "modulator" covers agonists, patrial agonists, antagonists and allosteric modulators of the nicotinic acetyl choline receptor (nAChR).

The compounds of the present invention exhibit a nicotinic pharmacology at least as good as nicotine itself, but preferably with lesser or even without the side effects associated with the use of nicotine. Moreover, the compounds of the invention are believed to have the potential as enhancers of neurotransmitter secretion, and suppress symptoms associated with a low activity of neurotransmitters.

The compounds of the present invention may in particular be characterised by having one or more of the following functionalities: A high binding selectivity for the receptor subtypes of neuronal nAChR's, in particular the α3 and/or the α7 subtype, binding selectivity for the serotonin receptor, a low affinity for the muscular subtype, an induction of cell survival, an oral efficacy in vivo of arousal/attention, a low toxicity in vivo, and by being non-mutagenic.

Due to their pharmacological profile the compounds of the invention may be useful for the treatment of diseases or conditions as diverse as CNS related diseases, diseases related to smooth muscle contraction, endocrine disorders, diseases related to neurodegeneratoin, disease related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction. Alzheimer's disease, attention deficit, attention deficit hyperactivity disorder, Parkinson'disease, Huntington's disease, Amyotrophic Lateral Sclerosis, Gilles de Ia Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's snydrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorder, or conditions associated with smooth muscle contractions, including convulsive disorders, angina pectoris, premature labour, convulsions, diarrhoea, asthma, epilepsy, trardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neurodegeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues. For this purpose the stannate derivatives of the are particularly useful.

Neuroimaging

The diazacycloalkane derivatives of the invention, in particular those being selective for the nicotinic receptor subtype α3, may be useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method a tracer comopund is a compound of the invention, or any of its enantiomers or any mixture thereof, or a pharmaceutically acceptable salt thereof, in labelled or unlabelled form.

In a preferred embodiment the physical detection method is selected from PET, SPECT; MRS, MRI, CAT, or combinations thereof.

The labelled compound of the invention preferably contains at least one radionuclide as a label. Positron emitting radionuclides are all candidates for usage. In the context of the invention the radionuclide is preferably selected from $^2$H (deutrium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc.

An examples of commercially available labelling agents, which can be used in the preparation of the labelled compounds of the present invention is [$^{11}$C]O$_2$, $^{18}$F, and NaI with different isotopes of Iodine.

In particular [$^{11}$C]O$_2$ may be converted to a [$^{11}$C]-methylating agent, such as [$^{11}$C]H$_3$I or [$^{11}$C]-methyl triflate.

Labelled compounds containing e.g. [$^{125}$I] labelled 1-iodoprop-1-en-3-yl as substituent on N-8 may be prepared as described in the art [Elmaleh, et al.; *J. Nucl. Med.* 1996 37 1197–1202].

Labelled compounds containing e.g. [$^{18}$F]-alkyl substituted N-8 may be prepared as described in the art, e.g. in WO 96/39198.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention labelled by incorporation of a isotope into the molecule, which may in particular be an isotope of the naturally occurring atoms including $^2$H (deuterium), $^3$H (tritium), $^{11}$C, $^{13}$C, $^{14}$C, $^{15}$O, $^{13}$N, $^{123}$I, $^{125}$I, $^{131}$I, $^{18}$F and $^{99m}$Tc, and the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diagnostically effective amount of the labelled or unlabelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semi-permeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five to ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispered homogeneously therein, as by stirring. The molten homogeneous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administering to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethan, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for examply by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be appropriate number of any of these in packaged form.

Tablets or capsules for oral administration and liquids for intravenous administration and continuous infusion are preferred compositions.

Further details on techniques for formulation and administration may be found in the latest edition of *Remingtion's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

The compounds of the present invention are valuable nAChR modulators and therefore useful for the treatment of a range of ailments invovling cholinergic dysfunction as well as a range of disorders responsive to the action of nAChR modulators as well as the serotonin receptor.

In another aspect the invention relates to the a method of the treatment or alleviation of a disease, disorder or condition of a living animal body, including a human, which disease, disorder or condition is responsive to the action of a nicotinic Acetyl Choline Receptor (nAChR) modulator, which method comprises the step of administering to such a living animal body, including a human, in need thereof a therapeutically effective amount of the chemical compound of the invention.

In the context of this invention the term "treating" covers treatment, prevention, prophylaxis or alleviation, and the term "disease" covers illnesses, diseases, disorders and conditions related to the disease in question.

In a preferred embodiment the disease or disorder to be treated is a disease or disorder of the central nervous system, a disease or disorder caused by or related to smooth muscle contraction, an endocrine disorder, a disease or disorder caused by or related to neuro-degeneration, a disease or disorder caused by or related to inflammation, pain, a withdrawal sympton caused by the termination of abuse of chemical substances.

In a more preferred embodiment the disease or disorder of the central nervous system is anxiety, cognitive disorders, learning deficit, memory deficits and dysfunction. Alzheimer's disease, attention deficit, attention deficit hyperactivity disorder. Parkinson's disease, Huntington's disease, Amyotrophic Lateral Sclerosis, Gilles de Il Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, chronic fatigue syndrome, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the disease or disorder caused by or related to smooth muscle contraction is convulsive disorders, angina pectoris, premature labour, convulsions, diarrhoea, asthma, epilepsy, tardive dyskinesia, hyperkinesia, premature ejaculation, and erectile difficulty.

In a third preferred embodiment the endocrine disorder is thyrotoxicosis, pheochromocytoma, hypertension and arrhythmias.

In a fourth embodiment the neuro-degenerative disease is transient anoxia and induced neurodegeneration.

In a fifth preferred embodiment the disease or disorder caused by or related to inflammation is an inflammatory skin disorder such as acne and rosacea, Chron's disease, inflammatory bowel disease, ulcerative colitis, and diarrhoea.

In a sixth preferred embodiment pain is a mild, a moderate or a severe pain of acute, chronic or recurrent character, a pain caused by migraine, a postoperative pain, or a phantom limb pain.

In a third preferred embodiment the addictive substance is a nicotine containing product such as tobacco, an opioids such as heroin, cocaine or morphine, a benzodiazepine or a benzodiazepine-like drug, or alcohol.

It is at present contemplated that a suitable dosages lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in change.

EXAMPLES

The invention is further illustrated in the following examples which are not intended to be in any way limiting to the scope of the invention as claimed.

All reactions involving air sensitive reagents or intermediates were performed under nitrogen and in anhyrous solvents. Magnesium sulphate is used as drying agent in the workup-procedures and solvents were evaporated under reduced pressure.

EXAMPLE 1

Pyridylpiperazines

Method A

4-Methyl-1-(3-Pyridyl)-Piperazine Fumaric Acid Salt (Compound 1A1)

A solution of 1-(3-pyridyl)-piperazine (0.35 g, 2.1 mmol), formic acid (1.0 g, 21.7 mmol), formaldehyde (0.64 g, 37%) and water (2 ml) was stirred at reflux for 15 hours. The mixture was evaporated and sodium hydroxide (30 ml, 1 M) was added and the product was extracted three times with ethyl acetate (15 ml). The corresponding salt was obtained by addition of a diethyl ether and methanol mixture (9:1) saturated with fumaric acid. Yield 0.21 g, 34% Mp. 144.5–145.9° C.

1-[5-(trans-Hex-2-en-1-yl-oxy-3-Pyridyl]-4-Methyl-Piperazine Fumaric Acid Salt (Compound 1A3)

Was prepared according to method A. Mp. 113.0–114.9° C.

Method B 1-(3-Pyridyl)-Piperazine Fumaric Acid Salt (Compound 1B1)

A solution of 1-(3-pyridyl)-4-tert-butoxycarbonylpiperazine (1.3 g, 4.9 mmol), trifluoroacetic acid (11.3 g, 99 mmol) and dichloromethane (50 ml) was stirred for 15 hours. The mixture was evaporated. Sodium hydroxide (30 ml, 4 M) was added. The product was extracted three times with dichloromethane (50 ml) and isolated as an oil. Yield 0.72 g, 90%. The corresponding salt was obtained by addition of a diethyl ether and methanol mixture (9:1), saturated with fumaric acid. Mp. 161.7–164.8° C.

Method C 1-(3-Pyridyl)-4-Tert-Butoxycarbonyl-Piperazine (Compound 1C1)

A mixture of 3-bromopyridine (7.8 g, 49.4 mmol), 1-tert-butoxycarbonylpiperazine (9.2 g, 49.4 mmol), tetrakis(triphenylphosphine)palladium(0) (286 mg, 0.247 mmol), potassium tert-butoxide (11.1 g, 98.8 mmol) and anhydrous toluene (100 ml) was stirred at 80° C. for 0.5 hours. Water (100 ml) was added and the mixture was extracted three times with ethyl acetate (75 ml). Chromatography on silica gel with dichloromethane, methanol and conc. ammonia (89:10:1) gave the title compound as an oil. Yield 1.34 g, 10%.

Method D 1-(5-Ethoxy-3-Pyridyl)Piperazine Fumaric Acid Salt (Compound 1D1)

A mixture of 3-chloro-5-ethoxypyridine (6.5 g, 45.8 mmol), piperazine (19.7 g, 229 mmol), potassium tert-butoxide (11.2 g, 91.6 mmol) and 1,2-dimethoxyethane (150 ml) was stirred at reflux for 1 hours. Aqueous sodium hydroxide (1 M, 100 ml) was added and the mixture was extracted two times with ethyl acetate (150 ml). Chromatography on silica gel with dichloromethane, methanol and conc. ammonia (89:10:1) gave the title compound. Yield 4.6 g, 48%. The corresponding salt was obtained by addition of a diethyl ether and methanol mixture (9:1) saturated with fumaric acid. Mp. 160.0–161.2° C.

1-[5-(Butoxy)-3-Pyridyl]-1,5-Diazacyclooctane Fumaric Acid Salt (Compound 1D2).

Was prepared according to methanol D, from 3-chloro-5-(butoxy)-pyridine, stirred at room temperature for 3 days. 1,5-Diazacyclooctane was prepared according to J. Hernandez-Mora "Derivatives of 1,5-diazacyclooctane" Ph.D. Dissertation, University of Michigan (1959). Mp. 146–148° C.

1-(5-Ethoxy-3-Pyridyl)-4-Ethyl-Piperazine Fumaric Acid Salt (Compound 1D3)

A mixture of 1-(5-ethoxy-3-pyridyl)-piperazine (1.4 g, 6.8 mmol), triethylamine (0.69 g, 6.8 mmol), bromoethane (0.88 g, 8.1 mmol) and dimethylformamide (25 ml). Aqueous sodium hydroxide (1 M, 50 ml) was added and the mixture was extracted two times with ethy acetate (50 ml). Chromatography on silica gel with dichloromethane, methanol and conc. ammonia (89:10:1) gave the title compound. Yield 0.75 g, 47%. The corresponding salt was obtained by addition of a diethyl ether and methanol mixture (9:1), saturated with fumaric acid. Mp. 144.8–145.9° C.

1-(5-Methoxy-3-Pyridyl)-4-Ethyl-Piperazine Fumaric Acid Salt (Compound 1D4)

Was prepared according to 1-(5-ethoxy-3-pyridyl)-4-ethyl-piperazine. Mp. 147.9–148.3° C.

4-Ethyl-1-(5-Propyloxy-3-Pyridyl)-Piperazine Fumaric Acid Salt (Compound 1D5)

Was prepared according to 1-(5-ethoxy-3-pyridyl)-4-ethyl-piperazine. Mp. 128.7–130.5° C.

EXAMPLE 2

Pyridylhomopiperazines

Method A

4-Methyl-1-(3-Pyridyl)-Homopiperazine (Compound 2A1)

A solution of 1-(3-pyridyl)-homopiperazine (0.42 g, 2.4 mmol), formic acid (3.3 g, 71.7 mmol), formaldehyde (2.1 g, 37%) and water (10 ml) was stirred at reflux for 15 hours. The mixture was evaporated and sodium hydroxide (15 ml, 4 M) was added and the product was extracted two times with ethyl acetate (15 ml). The product was obtained as an oil. Yield 0.46 g, 100%.

3,5-Bis-(N,N'-Homopiperazinyl)-Pyridine Fumaric Acid Salt (Compound 2A2)

Was prepared according to method A from 1-[5-(1-(4-tert-butoxycarbonylhomopiperazinyl))-3-pyridyl]homopiperazine. The corresponding salt was obtained by addition of a diethyl ether and methanol mixture (9:1), saturated with furmaic acid. Mp. 134–136° C.

4-Benzyl-1-(3-Pyridyl)-Homopiperazine Fumaric Acid Salt (Compound 2A3)

1-(3-Pyridyl)-homopiperazine (0.54 g, 3.0 mmol), potassium carbonate (0.42 g, 3.0 mmol), benzylbromide (0.56 g, 3.3 mmol) in dimethylformamide (40 ml) was stirred at 80° C. for one hour. Water (100 ml) was added and the mixture was extracted twice with ethyl acetate (25 ml). Yield 0.39 g, 49%. The corresponding salt was obtained by addition of a diethyl ether and methanol mixture (9:1), saturated with fumaric acid. Mp. 148.4–149.0° C.

1-(5-Ethoxy-3-Pyridyl)-4-Ethyl-Homopiperazine Fumaric Acid Salt (Compound 2A4)

Was prepared according to 4-benzyl-1-(3-pyridyl)-homopiperazine. Mp. 130.9–133.1° C.

1-(5-Ethoxy-3-Pyridyl)-4-Propyl-Homopiperazine Fumaric Acid Salt (Compound 2A5)

Was prepared according to 4-benzyl-1-(3-pyridyl)-homopiperazine. Mp. 96.5–97.5° C.

1-(5-Ethoxy-3-Pyridyl)-4-(Prop-2-En-1-Yl)-Homopiperazine Fumaric Acid Salt (Compound 2A6)

Was prepared according to 4-benzyl-1-(3-pyridyl)-homopiperazine at room temperature. Mp. 119.2–124.1° C.

Method B 1-(3-Pyridyl)-Homopiperazine Fumaric Acid Salt (Compound 2B1)

A solution of 1-(3-pyridyl)-4-tert-butoxycarbonylhomopiperazine (0.91 g, 3.3 mmol), trifluoroacetic acid (7.5 g, 66 mmol) and dichloromethane (30 ml) was stirred for 15 hours. The mixture was evaporated. Sodium hydroxide (30 ml, 4 M) was added. The product was extracted two times with dichloromethane (30 ml) and isolated as an oil. Yield 0.50 g, 85%. The corresponding salt was obtained by addition of a diethyl ether and methanol mixture (9:1) saturated with fumaric acid Mp. 172.1–172.9° C.

1-[5-(Propyl-1,2-Epoxy)-1-Oxy)-3-Pyridyl]-Homopiperazine (Compound 2B2)

Was prepared according to method B. Mp. 135.2–139.0° C.

1-(5-Phenylacetylenyl-3-Pyridyl)-Homopiperazine Fumaric Acid Salt (Compound 2B3)

Was prepared according to method B. Mp. 155.2–157.8° C.

1-(5,6-Dicholor-3-Pyridyl)-Homopiperazine Fumaric Acid Salt (Compound 2B4)

Was prepared according to method B. Mp. 172.2–173.4° C.

1-(6-Bromo-5-Chloro-3-Pyridyl)-Homopiperazine Fumaric Acid Salt (Compound 2B5)

Was prepared according to method B. Mp. 213–216° C.

1-(5,6-Dibromo-3-Pyridyl)-Homopiperazine Fumaric Acid Salt (Compound 2B6)

Was prepared according to method B. Mp. 192.1–193.2° C.

1-(5-Bromo-6-Chloro-3-Pyridyl)-Homopiperazine Fumaric Acid Salt (Compound 2B7)

Was prepared according to method B. Mp. 1882.–189.2° C.

Was prepared according to method B. Mp. 178–180° C.

1-(6-Bromo-5-Methoxy-3-Pyridyl)-Homopiperazine Fumaric Acid Salt (Compound 2B9)

Was prepared according to method B. Mp. 210–212° C.

1-(6-Bromo-5-Propyloxy-3-Pyridyl)-Homopiperazine Fumaric Acid Salt (Compound 2B10)

Was prepared according to method B. Mp. 154–155° C.

1-(6-Bromo-5-Vinyloxy-3-Pyridyl)-Homopiperazine Fumaric Acid Salt (Compound 2B11)

Was prepared according to method B. Mp. 128.6° C.

1-(6-Chloro-5-Vinyloxy-3-Pyridyl)-Homopiperazine Fumaric Acid Salt (Compound 2B12)

Was prepared according to method B. Mp. 183–185° C.

Method C 1-(3-Pyridyl)-4-Tert-Butoxycarbonylhomopiperazine (Compound 2C1)

A mixture of 3-bromopyridine (3.95 g, 25.0 mmol), 1-tert-butoxycarbonylhomopiperazine (5.0 g, 25.0 mmol), tetrakis(triphenylphosphine)palladium(0) 145 mg, 0.125 mmol), potassium tert-butoxide (6.1 g, 50.0 mmol) and anhydrous toluene 75 ml) was stirred at 80° C. for 4 hours. Water (100 ml) was added and the mixture was extracted three times with ethyl acetate (50 ml). Chromatography on silica gel with dichloromethane, methanol and conc. ammonia (89: 10:1) gave the title compound as an oil. Yield 0.92 g, 13%.

Method D 1-(5-Methoxy-3-Pyridyl)-Homopiperazine fumaric Acid Salt (Compound 2D1)

A mixture of 3-bromo-5-methoxypyridine (5.6 g, 30.0 mmol), homopiperazine (15.0 g, 150 mmol), tetrakis(triphenylphosphine)palladium(0) (173 mg, 0.15 mmol), potassium-tert-butoxide (6.7 g, 60 mmol) and anhydrous toluene (150 ml) was stirred at 80° C. for 4 hours. Water (100 ml) was added and the mixture was extracted seven times with ethyl acetate (150 ml). Chromatography on silica gel with dichloromethane, methanol and conc. ammonia (89:10:1) gave the title compound. Yield 3.5 g, 56%. The corresponding salt was obtained by addition of a diethyl ether and methanol mixture (9:1) saturated with fumaric acid. Mp. 161–162° C.

Method E

1-[(5-Methoxy-Methoxy)-3-Pyridyl]-Homopiperazine Fumaric Acid Salt (Compound 2E1)

A mixture of 3-chloro-5-methoxymethoxypyridine (10.0 g, 57.6 mmol), homopiperazine (28.8 g, 288 mmol), 1,3-bis-(diphenylphosphino)propanepalladiumdichloride (170 mg, 0.29 mmol), potassium tert-butoxide (12.9 g, 115 mmol) and 1,2-dimethoxyethane (100 ml) was stirred at reflux for 3 hours. Sodium hydroxide (1 M, 100 ml) was added and the mixture was extracted two times with ethyl acetate (150 ml). Chromatography on silica gel with dichloromethane, methanol and conc. ammonia (89:10:1) gave the title compound as free base. Yield 9.7 g, 71%. The corresponding salt was obtained by addition of a diethyl ether and methanol mixture (9:1) saturated with fumaric acid. Mp. 129.5–131° C.

Method F 1-(5-(1-Pyrrolyl)-3-Pyridyl)-Homopiperazine Fumaric Acid Salt (Compound 2F1)

A mixture of 3-chloro-5-(1-pyrrolyl)-pyridine (6.3 g, 35.3 mmol), homopiperazine (7.06 g, 70.5 mmol), potassium tert-butoxide (7.19 g, 70.5 mmol) and 1,2-dimethoxyethane (100 ml) was stirred at reflux for 3 hours. Sodium hydroxide (1 M, 120 ml) was added and the mixture was extracted three times with ethyl acetate (100 ml). Chromatography on silica gel with dichloromethane, methanol and conc. ammonia (89:10:1) gave the title compound. Yield 3.45 g, 40%. The corresponding salt was obtained by addition of a diethyl ether and methanol mixture (9:1) saturated with fumaric acid. Mp. 174–175° C.

1-[5-(2-Ethyl-1-Butoxy)-3-Pyridyl]-Homopiperazine Fumaric Acid Salt (Compound 2F2)

Was prepared according to method F. Mp. 113.7–115.9° C.

1-[5-(Methyl-1-Prop-2-En-Oxy)-3-Pyridyl]-Homopiperazine Fumaric Acid Salt (Compound 2F3)

Was prepared according to method F. Mp. 129.5–133.6° C.

1-[5-(Cyclobutylmethoxy)-3-Pyridyl]-Homopiperazine Fumaric Acid Salt (Compound 2F4)

Was prepared according to method F. Mp. 158.9–159.9° C.

1-[5-(Hex-2-En-Oxy)-3-Pyridyl]-Homopiperazine Fumaric Acid Salt (Compound 2F5)

Was prepared according to method F. Mp. 126.8–130.2° C.

1-[5-(2-Methyl-1-Prop-1-En-Oxy)1-En-Oxy)-3-Pyridyl]-Homopiperazine Fumaric Acid Salt (Compound 2F6)

Was prepared according to method F, with reflux for 3 days to ensure complete isomerisation of the double bond from 1-[5-(1-Methyl-1-prop-2-en-oxy)-3- pyridyl]homopiperazine. Mp. 114.4–116.0° C.

1-[5-(N-Butyl-N-Methylamino)-3-Pyridyl]-Homopiperazine Fumaric Acid Salt (Compound 2F7)

Was prepared according to method F. Mp. 140.5–141.8° C.

1-[5-(N-Pyrrolidinyl)-3-Pyridyl]-Homopiperazine Fumaric Acid Salt (Compound 2F8)

Was prepared according to method F. Mp. 141.5–143.0° C.

1-[5-(N-Azetidinyl)-3-Pyridyl]-Homopiperazine Fumaric Acid Salt (Compound 2F9)

Was prepared according to method F. Mp. 143.5–146.9° C.

1-[5-(1-(4-Tert-Butoxycarbonylhomopiperazinyl))-3-Pyridyl]-Homopiperazine Fumaric Acid Salt (Compound 2F10)

Was prepared according to method F from 1-(5-chloro-3-pyridyl)-4-tert- butoxycarbonylhomopiperazine. Mp. 184–186° C.

1,4-Bis-[5-Ethoxy-3-Pyridyl]-Homopiperazine Fumaric Acid Salt (Compound 2F11)

Was prepared according to method F as the minor product. Mp. 155–156° C.

1,4-Bis-[5-(1-Propyl-1-En-Oxy)-3-Pyridyl]-Homopiperazine Fumaric Acid Salt (Compound 2F12)

Was prepared according to method F as the minor product. Mp. 156–158° C.

1,4-Bis-[5-(Vinyl-Oxy)-3-Pyridyl]-Homopiperazine Fumaric Acid Salt (Compound 2F13)

Was prepared according to method F as the minor product. Mp. 157–158.5° C.

1-(5-Bromo-3-Pyridyl)-4-Tert-Butoxycarbonylhomopiperazine (Compound 2F14)

A mixture of 1-(5-bromo-3-pyridyl)-homopiperazine (19.0 g, 74.2 mmol), and di-tert-butyl dicarbonat (16.2 g, 74.2 mmol), triethylamine (7.5 g, 74.2 mmol) and dichloromethane (200 ml) was stirred at room temperature for 1 hours. The crude mixture was purified by chromatography on silica gel using ethyl acetate:petroleum (1:1) as solvent. Yield 16.6 g, 55%.

1-(5-Chloro-3-Pyridyl)-4-Tert-Butoxycarbonylhomopiperazine (Compound 2F15)

Was prepared from 1-(5-Chloro-3-pyridyl)-homopiperazine according to 1-(5-Bromo-3- pyridyl)-4-tert-butoxycarbonyl-homopiperazine.

1-(5-Phenylacetylenyl-3-Pyridyl)-4-Tert-Butoxycarbonyl-homopiperazine (Compound 2F16)

A mixture of 1-(5-bromo-3-pyridyl)-4-tert-butoxycarbonyl-homopiperazine (3.5 g, 9.8 mmol), phenylacetylene (2.0 g, 19.6 mmol), tetrakis(triphenylphosphine)palladium(0) (100 mg, 0.086 mmol), diethylamine (1.4 g, 19.6 mmol) and tetrahydrofuran (50 ml) was refluxed for 5 hours. Aqueous sodium hydroxide (75 ml, 1M) was added. the mixture was extracted twice with ethyl acetate. The mixture was purified by chromatography on silica gel using ethyl acetate:petroleum (1:1) as solvent. Yield 0.54 g, 7.3%.

1-(5,6-Dichloro-3-Pyridyl)-4-Tert-Butoxycarbonylhomopiperazine (Compound 2F17)

A mixture of 1-(5-chloro-3-pyridyl)-4-tert-butoxycarbonyl-homopiperazine (1.56, 5.0 mmol), 1,3-dichloro-5,5-dimethylhydantion (0.985 g, 5.0 mmol) and dichloromethane (50 ml) was stirred for 180 minutes. The crude mixture was evaporated and purified by chromatography on silica gel using ethyl acetate:petroleum (3:1) as solvent. Yield 0.46 g, 27%.

1-(6-Bromo-5-Chloro-3-Pyridyl)-4-Tert-Butoxycarbonyl-homopiperazine (Compound 2F18)

A mixture of 1-(5-chloro-3-pyridyl)-4-tert-butoxycarbonyl-homopiperazine (2.34 g, 7.5 mmol), N-bromosuccinimide (1.34 g, 7.5 mmol) and acetonitrile (75 ml) was stirred for 60 minutes. The crude mixture was evaporated and purified by chromatography on silica gel using ethyl acetate:petroleum (2:1) as solvent. Yield 2.5 g, 85%.

1-(5,6-Dibromo-3-Pyridyl)-4-Tert-Butoxycarbonylhomopiperazine (Compound 2F19)

A mixture of 1-(5-bromo-3-pyridyl)-4-tert-butoxycarbonyl-homopiperazine (2.68 g, 7.5 mmol), N-bromosuccinimide (1.34 g, 7.5 mmol) and acetonitrile (75 ml) was stirred for 30 minutes. The crude mixture was evaporated and purified by chromatography on silica gel using ethyl acetate:petroleum (2:1) as solvent. Yield 3.0 g, 92%.

1-(5-Bromo-6-Chloro-3-Pyridyl)-4-Tert-Butoxycarbonyl-homopiperrazine (Compound 2F2)

A mixture of 1-(5-bromo-3-pyridyl)-4-tert-butoxycarbonyl-homopiperazine (2.68 g, 7.5 mmol), 1,3-dichloro-5,5-dimethylhydantoin (0.89 g, 4.5 mmol) and acetonitrile (75 ml) was stirred for 45 minutes. The crude mixture was evaporated and purified by chromatography on silica gel using ethyl acetate:petroleum (2:1) as solvent. Yield 0.80 g, 51%.

Method G 1-(6-Chloro-3-Pyridazinyl)-Homopiperazine Fumaric Acid Salt (Compound 2G1)

A mixture of 3,6-dichloropyridazine (5.0 g, 33.5 mmol), homopiperazine (3.36 g, 33.5 mmol) and 50 ml of toluene was stirred at reflux for 0.5 h. Sodium hydroxide (50 ml, 1M) was added and the mixture was extracted three times with ethyl acetate (100 ml). Chromatography on silica gel with dichloromethane, methanol and conc. ammonia(89:10:1) gave the title compound as free base. Yield 2.2 g, 31%. the corresponding salt was obtained by addition of a diethyl ether and methanol mixture (9:1) saturated with fumaric acid. Mp. 165–166° C.

1-(6-Bromo-3-Pyridazinyl)-1,5-Diazacyclooctane Fumaric Acid Salt (Compound 2G2)

Was prepared according to method G, using dioxane at reflux. 3,6-Dibromopyridazine [Coad P, Coad R A, Clough S, Hyepock J, Salisbury R and Wilinks C; J. Org. Chem. 1963 28 218–221] and 1,5-diazacyclooctane was used as starting material Mp. 164.5–166.5° c.

1-(6-Bromo-3-Pyridazinyl)-Homopiperazine Fumaric Acid Salt (Compound 2G3)

Was prepared according to method G. Mp. 169–171° C.

Method H 1-(3-Pyridazinyl)-Homopiperazine (Compound 2H1)

A mixture of 1-(3-chloro-6-pyridazinyl)-homopiperazine (5.56 g, 26.1 mmol), palladium on carbon (2.1 g, 10%) and ethanol (150 ml) was stirred under hydrogen overnight. The crude product was filtered through celite and evaporated. Chromatography on silica gel with dichloromethane, methanol and conc. ammonia (89:10:1) gave the title compound as free base. Yield 2.78 g, 60%, 185.0–186.9° C.

1-[5-Phenyl-2-eth-1-yl-3-pyridyl]-homopiperazine fumaric acid salt (Compound 2H2)

Was prepared from 1-(5-phenylacetylenyl-3-pyridyl) homopiperazine according to method H. Mp. 135.8–138.6° C.

1-[5-Ethyl-3-pyridyl]-homopiperazine fumaric acid salt (Compound 2H3)

Was prepared from 1-(5-ethynyl-3-pyridyl) homopiperazine according to method H. Mp. 122.8–124.6° C.

1-[5-(Propyl-1-en-oxy)-3-pyridyl]-4-tert-butoxycarbonyl-homopiperazine (Compound 2H4)

A mixture of 1-[5-(propyl-1-en-oxy)-3-pyridyl]-homopiperazine (5.0 g, 21.7 mmol), tert-butoxycarbonyl anhydride (5.7 g, 26.0 mmol), triethylamine (4.4 g, 43.4 mmol) and dichloromethane (100 ml) was stirred 1 h at room temperature. The organic phase was washed twice with an aqueous mixture of sodium hydroxide (50 ml, 1 M). Chromatography on silica gel with dichloromethane and methanol (19:1) gave the title compound as free base as an oil. Yield 5.9 g, 82%.

1-[5-(Propyl-1,2-epoxy-1-oxy)-3-pyridyl]-4-tert-butoxycarbonyl-homopiperzine (Compound 2H5)

A mixture of 1-[5-(propyl-1-en-oxy)-3-pyridyl]-4-tert-butoxycarbonyl-homopiperazine (2.0 g, 5.7 mmol), m-chloroperbenzoic acid (1.3 g, 7.4 mmol) and chloroform (75 ml) was stirred at room temperature for 2 hours. Sodium hydroxide (150 ml, 1 M) was added, the aqueous phase was discarded and the organic phase was washed with sodium hydroxide (100 ml, 1 M). Chromatography on silica gel with dichloromethane, methanol and conc. ammonia (89:10:1) gave the title compound as free base. Yield 0.89 g, 45%.

Method I 1,4-[α,α'-Bis-(5-Ethoxy-3-pyridyl-1-homopiperazinyl)]-dimethylbenzene fumaric acid salt (Compound 2I1)

To a mixture of 1-(5-ethoxy-3-pyridyl)-homopiperazine (5.0 g, 22.6 mmol), triethylamine (2.1 g, 20.6 mmol) and ethanol (50 ml): was added α,α'-dibromo-p-xylene (2.7 g, 10.3 mmol) at room temperature. The mixture was stirred overnight at room temperature. The crude mixture was evaporated and purified by chromatography on silica gel with dichloromethane, methanol and conc. ammonia (89:10:1) gave the title compound as free base. Yield 0.84 g, 15%. The corresponding salt was obtained by addition of a diethyl ether and methanol mixture (9:1) saturated with fumaric acid. Mp. 173.0–174.9° C.

1,4-[α,α'-Bis-(6-Chloro-3-pyridazinyl-1-homopiperazinyl)]-dimethylbenzene fumaric acid salt (Compound 2I2)

Was prepared according to method I. Mp. 201–202° C.

O,O'-Bis-[5-(1-homopiperazinyl)-3-pyridyl]-ethyleneglycol fumaric acid salt (Compound 2I3)

A mixture of O,O'-Bis-(5-chloro-3-pyridyl)-ethyleneglycol (3.0 g, 10.6 mmol), homopiperazine (5.3 g, 52.8 mmol), potassium-tert-butoxide (5.9 g, 52.8 mmol) and 1,2-dimethoxyethane (30 ml) was stirred at room temperature overnight. Aqueous sodium hydroxide (50 ml) was added and the mixture was extracted three times with ethyl acetate (30 ml). The crude mixture was evaporated and purified by chromatography on silica gel with dichloromethane, methanol and conc. ammonia (79:20:1) gave the title compound as free base. Yield 0.57 g, 13%. The corresponding salt was obtained by addition of a diethyl ether and methanol mixture (9:1) saturated with fumaric acid. Mp. 168–171° C.

O,O'-Bis-(5-chloro-3-pyridyl)-ethyleneglycol (Compound 2I4)

(Reactant to O,O'-Bis-[5-(1-homopiperazinyl)-3-pyridyl] ethyleneglycol)

A mixture of ethyleneglycol (138.4 g, 2.23 mol) and sodium (12.3 g, 0.53 mol) was stirred at 80° C. for 4 hours. 3,5-Dichloropyridine (66.0 g, 0.45 mol) and dimethyl sulfoxide (300 ml) was stirred at 110° C. for 10 hours. The mixture was allowed to reach room temperature. Aqueous sodium hydroxide (1 M, 600 ml) was added, the mixture was stirred and filtered. The title compound was isolated as a crystalline product was ioslated (8.7 g, 6.8%). Mp. 136–138° C.

1-[3-(4-Chloro-1,2,5-thiadiazolyl)]homopiperazine fumaric acid salt (Compound 2I5)

A mixture of 3,4-dichloro-1,2,5-thiadiazole (5.0 g, 32.3 mmol) and homopiperrazine (6.47 g, 64.6 mmol), in the absence of solvent, was stirred at 110° C. for 30 minutes. Aqueous sodium hydroxide (1 M, 100 ml) was added. The mixture was extracted with diethyl ether (3×50 ml). The crude mixture was evaporated and purified by chromatography on silica gel with dichloromethane, methanol and conc. ammonia (89:10:1) gave the title compound as free base. The corresponding salt was obtained by addition of a diethyl ether and methanol mixture (9:1) saturated with fumaric acid. Yield 6.3 g, 58%. Mp. 180–181° C.

1-[6-Iodo-3-pyridazinyl]-homopiperazine fumaric acid salt (Compound 2I6)

Was prepared in the same way as 1-[3-(4-Chloro-1,2,5-thiadiazolyl)]-homopiperazine above from 3,6-diiodopyridazine in the presence of dioxane for 5 hours. Mp. 182.5–185° C.

Method J 1-(5-Chloro-3-pyridyl)-homopiperazine fumaric acid salt (Compound 2J1)

A mixture of 3,5-dichloropyridine (50.0 g, 337.9 mmol) and homopiperazine (67.7 g, 675.7 mmol) was stirred for 40 h at 150° C. in the absence of solvent. The pH was adjusted to 6 by adding hydrochloric acid (4 M, 250 ml). The aqueous phase was washed two times with ethyl acetate (2×300 ml). Aqueous sodium hydroxide (4 M, 250 ml) was added. The alkaline water phase was extracted five times with diethyl ether (5×250 ml). The mixture was evaporated. Yield 29.0 g, 40%. The corresponding salt was obtained by addition of a diethyl ether and methanol mixture (9:1, 400 ml) with fumaric acid (16.7 g). Mp. 179–180° C.

1-(5-Bromo-3-pyridyl)-homopiperazine fumaric acid salt (Compound 2J2)

Was prepared according to method J. The mixture was stirred overnight at 140° C. Mp. 186–187° C.

1-[5-Chloro-3-pyridyl]-1,5-diazacyclooctane fumaric acid salt (Compound 2J3)

Was prepared according to method J. Mp. 186–187° C.

1-[5-Bromo-3-pyridyl]-1,5-diazacyclooctane fumaric acid salt (Compound 2J4)

Was prepared according to method J. Mp. 151–153° C.

1-(5-Iodo-3-pyridyl)-4-tert-butoxycarbonyl-homopiperazine (Compound 2J5)

Starting material to 1-(5-iodo-3-pyridyl)-homopiperazine. A mixture of Iodomono chloride (588 mg, 3.6 mmol) and anhydrous dichloromethane (10 ml) was added to a mixture of 1-(5-trimethylstannyl-3-pyridyl)-4-tert-butoxycarbonyl-homopiperazine (1.45 g, 3.3 mmol) and dichloromethane (30 ml). the mixture was stirred at room temperature for 1 hours. Aqueous sodium hydroxide (25 ml, 1 M) was added. The organic phase was separated. The aqueous phase was extracted with dichloromethane (25 ml). The combined organic phases was purified by chromatography on silica gel with dichloromethane and methanol (19:1) The title compound was isolated as an oil. Yield 0.80 g, 60%.

1-(5-Trimethylstannyl-3-pyridyl)-4-tert-butoxycarbonyl-homopiperazine (Compound 2J6)

A mixture of 1-(5-bromo-3-pyridyl)-4-tert-butoxycarbonyl-homopiperazine (3.5 g, 9.82 mmol), tetrakis(triphenylphosphine)palladium(0) (0.12 g, 0.10 mmol), hexamethylditin (5.0, 15.3 mmol) and 1,2-dimethoxyethane (50 ml) was heated at reflux for 2 hours. Aqueous sodium hydroxide (50 ml, 0.5 M) was added. The mixture was extracted twice with diethyl ether (2×50 ml). The combined organic phases was purified by chromatography on silica gel with dichloromethane and methanol (16:1) gave the title compound as an oil. Yield 4.0 g, 92%.

Method K 1-(6-Bromo-5-methoxy-3-pyridyl)-4-(tert-butoxycarbonyl)-homopiperazine (Compound 2K1)

Bromosuccinimide (3.56 g, 20.0 mmol) was added to a mixture of 1-(5-methoxy-3- pyridyl)-4-tert-butoxycarbinyl homopiperazine (6.14 g, 20.0 mmol) and acetonitrile (200 ml) at room-temperature and stirred for 20 minutes. the mixture was evaporated and purified by chromatography on silica gel with ethyl acetate and petroleum (1:1) as solvent and gave 4.4 g, 57% of the title compound.

1-(6-Bromo-5-propyloxy-3-pyridyl)-4-(tert-butoxycarbonyl)-homopiperazine (Compound 2K2)

was prepared according to method K.

1-(6-Bromo-5-vinyloxy-3-pyridyl)-4-(tert-butoxycarbonyl)-homopiperazine (Compound 2K3)

was prepared according to method K.

1-(6-Chloro-5-vinyloxy-3-pyridyl)-4-(tert-butoxycarbonyl)-homopiperazine (Compound 2K4)

was prepared according to method K using 1,3-dichloro-5,5-dimethylhydantoin as chlorinating agent.

1-(3-Pyridyl)-1,5-diazacyclooctane fumaric acid salt (Compound 2K5)

3-Fluoropyridine (3.0 g, 30.9 mmol), 1,5-diazacyclooctane (9.88 g, 30.9 mmol) and 1,4-dioxane (3 ml) was heated to 160° C. in a sealed vessled for 18 hours. Aqueous sodium hydroxide (50 ml, 1M) was added and the mixture was extracted with ethyl acetate (3×40 ml). Purification by column chromatography yielded 5% of the title compound (0.30 g, 1.6 mmol) as an oil, which was converted to the corresponding fumaric acid salt. Mp. 137.7–141.1° C.

Homopiperazinyl-5-pyrid-3-yl-5-pyrid-3-yl-homopiperazine fumaric acid salt (Compound 2K6)

1-(5-bromo-3-pyridyl)-homopiperazine (7.82 g, 30.5 mmol), hexamethyldtin (5.17 g, 15.3 mmol) and tetrakis(triphenylphosphine)palladium(0) (0.35 g, 0.3 mmol) was dissolved in 1,4-dioxane and heated at 100° C. for 48 h in an inert atmosphere. Additional tetrakis(triphenylphosphine)palladium(0) (0.35 g, 0.3 mmol) was added at room temperature and heating was continued for another 24 hours. Aqueous sodium hydroxide (25 ml, 1M) was added and the mixture was extracted with methylene chloride. Purification by column chromatography afforded 63% of the product (3.38 g, 9.6 mmol) as an oil, which was converted to the corresponding fumaric acid salt. Mp. 216.1° C.

1-(6-Chloro-3-pyridyl)-homopiperazine fumaric acid salt (Compound 2K7)

1-(6-Amino-3-pyridyl)-homopiperazine (96 mg, 0.5 mmol) was solved in conc. hydrochloric acid (2.0 ml). Sodium nitrite (45 mg, 0.65 mmol) was added at 0° C. The mixture was allowed to reach room-temperature and was stirred overnight. The mixture was poured out on water (20 ml) and was refluxed for 10 minutes. The mixture was made alkaline by adding aqueous sodium hydroxide (1.0 ml, 4 M). The mixture was extracted with ehtyl acetate (3×10 ml). The product was isolated as an oil. Yield 50 mg (47%). The free base was converted to the correspondong fumaric acid salt. Mp. 165–167° C.

1-(6-Amino-3-pyridyl)-homopiperazine fumaric acid salt (Compound 2K8)

1-(6-Nitro-3-pyridyl)-homopiperazine (1.5 g, 6.8 mmol), platinum dioxide (100 mg) and ethanol (200 ml, 99%) was stirred under hydrogen for 45 minutes until the theoretical volume (454 ml) was consumed. The crude mixture was filtered through celite. The mixture was purified by silica-column chromatography, using a mixture of methylene chloride:methanol (9:1) and 1% of ammonia as solvent. Yield 1.1 g (85%). The corresponding salt was obtained by addition of a diethyl ether and methanol mixture (9:1) saturated with fumaric acid. Mp. 120–122° C.

1-(6-Nitro-3-pyridyl)-homopiperazine fumaric acid salt (Compound 2K9)

3-Bromo-6-nitro-pyridine (1.4 g, 6.9 mmol) and homopiperazine (2.1 g, 21 mmol) was mixed and stirred for 45 minutes at 70° C. The crude mixture was evaporated and purified by silica-column chromatography, using a mixture of methylene chloride:methanol (9:1) and 1% of ammonia as solvent. Yield 1.2 g (78%). The corresponding salt was obtained by addition of a diethyl ether and methanol mixture (9:1) saturated with fumaric acid. Mp. 223–225° C.

3-Bromo-6-nitro-pyridine (Compound 2K10)

Conc. sulphuric acid (90 ml) was added to hydrogen peroxide (60 ml, 10%) at 0° C. A mixture of 2-amino-5-bromopyridine (8.7 g, 50 mmol) and conc. sulphuric acid (120 ml) was added slowly at 0° C. The mixture was stirred at room temperature for 18 hours. The crude mixture was poured out on ince and crystals precipitated. The crystals were combined with sodium hydroxide (100 ml, 1M) and methylene chloride (100 ml). The product (according to GC-MS) was isolated from the organic phase. Yield 6.1 g (60%) Mp. 146–148° C.

EXAMPLE 3

Biological Activity

Nicotinic acetyl choline receptors in the brain are pentameric structures composed of subunits distinct from those found in skeletal muscles. The existence of seven $\alpha$-subunits ($\alpha 2$–$\alpha 7$, $\alpha 9$) and three $\beta$-subunits ($\beta 2$–$\beta 4$) in the mammalian brain has been described.

The predominant subtype with high affinity for nicotine is comprised of $\alpha_4$ and $\beta_2$ subunits.

The affinity of compounds of the invention for nicotinic acetyl choline receptors have been investigated in three test for in vitro inhibition of $^3$H-epibatidine binding, $^3$H-$\alpha$-bungarotoxine binding and $^3$H-cytisine binding as described below.

In vitro inhibition of $^3$H-cytisine binding (Assay I)

The predominant subtype with high affinity for nicotine is comprised of $\alpha_4$ and $\beta_2$ subunits nAChRs of the latter type can selectively be labelled by the nicotine agonist $^3$H-cytisine.

Tissue Preparation

Preparations are performed at 0–4° C. unless otherwise indicated. Cerebral corticies from male Wistar rates (150–250 g) are homogenised for 20 seconds in 15 ml Tris, HCI (50 mM, pH 7.4) containing 120 mM NaCI, 5 mM KCI, 1 mM $MgCl_2$ $_{l\ and}$ 2.5 mM $CaCl_2$ using an Ultra-Turrax homogeniser. The homogenate is centrifuged at 27,000× g for 10 minutes. The supernatant is discarded and the pellet is resuspended in fresh buffer and centrifuged a second time. The final pellet is resuspended in fresh buffer (35 ml per g of original tissue) and used for binding assays.

Assay

Aliquots of 500 µl homogenate are added to 25 µl of test solution and 25 µl of $^3$H-cytisine (1 nM, final concentration), mixed and incubated for 90 minutes at 2° C. Non-specific binding is determined using (−)-nicotine (100 µM, final concentration). After incubation the samples are added 5 ml of ice-cold buffer and poured directly onto Whatman GF/C glass fibre fitlers under suction and immediately washed with 2×5 ml ice-cold buffer. The amount of radioactivity on the filters is determined by conventional liquid scintillation counting. Specific binding is total binding minus non-specific binding.

In vitro inhibition of $^3$H-epibatidine binding (Assay II)

Epibatidine is an alkaloid that was first isolated from the skin of the Ecuadoran frog *Epipedobates tricolor* and was found to have very high affinity for neuronal nicotinic receptors, where it acts as a potent agonist. $^3$H-epibatidine binds to two sites in rat brain, both of which have pharmacological profiles consistent with neuronal nicotinic receptors and a similar brain regional distribution [Hougling et al.; *Mol. Pharmacol.* 1995 48 280–287].

The high affinity binding site for $^3$H-epibatidine is most certainly binding to the $\alpha_4\beta_2$ subtype of nicotinic receptors. The identity of the low affinity site is still unknown; does it represent a second nicotinic receptor or a second site in the same receptor. The ability of α-bungarotoxine to compete for $^3$H-epibatidine binding sites indicates that neither site measured represents the nicotinic receptor composed of $\alpha_7$ subunits.

Tissue Preparation

Preparations are performed at 0–4° C. unless otherwise indicated. The forebrain (+ cerebellum) from a male Wistar rat (150–250 g) is homogenised for 10–20 seconds in 20 ml Tris, HCl (50 mM, pH 7.4) using an Ultra-Turrax homogeniser. The tissue suspension is centrifuged at 27,000 × g for 10 minutes. The supernatant is discarded and the pellet is washed three times by centrifugation at 27,000 × g for 10 minutes in 20 ml fresh buffer, and the final pellet is resuspended in fresh buffer (400 ml per g of original tissue) and used for binding assays.

Assay

Aliquots of 2.0 ml homogenate are added to 0.100 ml of test solution and 0.100 ml of $^3$H-epibatidine (0.3 nM, final concentration), mixed and incubated for 60 minutes at room temperature. Non-specific binding is determined using (−)-nicotine (30 µM, final concentration). After incubation the samples are poured directly onto Whatman GF/C glass fibre filters (pre-soaked in 0.1% PEI for at least 20 min) under suction and immediately washed with 2×5 ml ice-cold buffer. The amount of radioactivity on the filters is determined by conventional liquid scintillation counting. Specific binding is total binding minus non-specific binding.

In vitro inhibition of $^3$H-α-bungarotoxine binding Rat Brain (Assay III)

α-Bungarotoxine is a peptide isolated from the venom of the Elapidae snake *Bungarus multicinctus* [Mebs et al.; *Biochem. Biophys. Res. Commun.* 1971 44 (3) 711], and has high affinity for neuronal and neuromusculr nicotinic receptors, where it acts as a potent antagonist. $^3$H-α-Bungarotoxine binds to a single site in rate brain with an unique distribution pattern in rat brain [Clarke et al.; *J. Neurosci.* 1985 5 1307–1315].

$^3$H-α-Bungarotoxine labels nAChR formed by the $\alpha_7$ subunit isoform found in brain and the $\alpha_1$ isoform in the neuromuscular junction [Changeaux; *Fidia Res. Found. Neurosci. Found. Lect.* 1990 4 21–168]. Functionally, the $\alpha_7$ homo-oligomer expressed in oocytes has a calcuim permeability greater than neuromuscular receptors and, in some instances greater than NMDA channels [Seguela et al.; *J. Neurosci.* 1993 13 596–604].

Tissue Preparation

Preparations are performed at 0–4° C. unless otherwise indicated. Cerebral cortices from male Wistar rates (150–250 g) are homogenised for 10 seconds in 15 ml 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is centrifuged at 27,000 × g for 10 minutes. The supernatant is discarded and the pellet is washed twice by centrifugation at 27,000 × g for 10 minutes in 20 ml fresh buffer, and the final pellet is resuspended in fresh buffer containing 0.01% BSA (35 ml per g or original tissue) and used for binding assays.

Assay

Aliquots of 500 µl homogenate are added to 25 µl of test solution and 25 µl of $^3$H-α-bungarotoxine (2 nM, final concentration), mixed and incubated for 2 h at 37° C. Non-specific binding is determined using (−)-nicotine (1 mM, final concentration). After incubation the samples are added 5 ml of ice-cold Hepes buffer containing 0.05% PEI and poured directly onto Whatman GF/C glass fibre filters (pre-soaked in 0.1% PEI for at least 6 h) under suction and immediately washed with 2×5 ml ice-cold buffer. The amount of radioactivity on the filters is determined by conventional liquid scintillation counting. Specific binding is total binding minus non-specific binding.

The results of these experiments are presented in Table 1 below.

TABLE 1

In vitro Binding Activity

| Compound | Assay I IC$_{50}$ (µM) | Assay II IC$_{50}$ (µM) | Assay III IC$_{50}$ (µM) |
|---|---|---|---|
| 1-[5-(Butoxy)-3-pyridyl]-1,5-diazacyclooctane fumaric acid salt | 0.002 | 0.003 | 30.0 |
| 1-(5-Methoxy-3-pyridyl)-4-ethyl-piperazine fumaric acid salt | 0.46 | 0.71 | 30.0 |
| 4-Ethyl-1-(5-propyloxy-3-pyridyl)-piperazine fumaric acid salt | 0.12 | 0.38 | 30.0 |
| 1-(5-Ethoxy-3-pyridyl)-4-ethyl-homopiperazine fumaric acid salt | 0.061 | 0.37 | >30.0 |

TABLE 1-continued

In vitro Binding Activity

| Compound | Assay I IC$_{50}$ (μM) | Assay II IC$_{50}$ (μM) | Assay III IC$_{50}$ (μM) |
|---|---|---|---|
| 1-(5-Ethoxy-3-pyridyl)-4-propyl-homopiperazine fumaric acid salt (NS3966) | 0.26 | 1.6 | 85.0 |
| 1-(5-Ethoxy-3-pyridyl)-4-(prop-2-en-1-yl-) homopiperazine fumaric acid salt | 0.037 | 0.23 | >30.0 |
| 1-[5-(Propyl-1,2-epoxy-1-oxy)-3-pyridyl]-homopiperazine | 0.023 | 0.040 | 58.0 |
| 1-(5-Phenylacetylenyl-3-pyridyl) homopiperazine fumaric acid salt | 0.007 | 0.005 | 11.0 |
| 1-(5,6-Dichloro-3-pyridyl)-homopiperazine fumaric acid salt | 0.004 | 0.002 | <3.0 |
| 1-(6-Bromo-5-chloro-3-pyridyl)-homopiperazine fumaric acid salt | 0.001 | 0.002 | <3.0 |
| 1-(5,6-Dibromo-3-pyridyl)-homopiperazine fumaric acid salt | 0.001 | 0.001 | 3.0 |
| 1-(5-Bromo-6-chloro-3-pyridyl)-homopiperazine fumaric acid salt | <0.030 | 0.001 | <3.0 |
| 1-[5-(2-Ethyl-1-butoxy)-3-pyridyl]homopiperazine fumaric acid salt | 0.004 | 0.013 | >30.0 |
| 1-[5-(1-Methyl-1-prop-2-en-oxy)-3-pyridyl]homopiperazine fumaric acid salt | 0.011 | 0.052 | 11.0 |
| 1-[5-(Cyclobutylmethoxy)-3-pyridyl]homopiperazine fumaric acid salt | 0.001 | 0.004 | >30.0 |
| 1-[5-(Hex-2-en-oxy)-3-pyridyl]homopiperazine fumaric acid salt | 0.006 | 0.008 | 47.0 |
| 1-[5-(2-Methyl-1-prop-1-en-oxy)-3-pyridyl]homopiperazine fumaric acid salt | 0.022 | 0.020 | 85.0 |
| 1-[5-(N-Butyl-N-methylamino)-3-pyridyl]homopiperazine fumaric acid salt | 0.28 | 0.27 | 85.0 |
| 1-[5-(N-pyrrolidinyl)-3-pyridyl]homopiperazine fumaric acid salt | 0.008 | 0.040 | 5.0 |
| 1-(6-Bromo-3-pyridazinyl)-homopiperazine fumaric acid salt | 0.020 | 0.070 | 1.5 |

These results show the excellent binding affinity and selectivity of the compounds of the invention for the nicotinic acetyl choline receptors, in particular the nAchR subtypes α4β2.

The invention claimed is:

1. The dimeric diazacycloalkane represented by Formula II, III, or IV (II)

(III)

(IV)

any of its enantiomers or any mixture thereof, an N oxide thereof, a pharmaceutically acceptable salt thereof, in a labelled or un-labelled form, wherein, n is 1; and m is 2; and R represents hydrogen, an alkyl group, a cycloalkyl group, a cycloalkylalkyl group, or an alkenyl group, or, when R is shown with two valences, R represents an alkylene group, a cycloalkylene group, a cycloalkylalkylene group, or an alkenylene group; and $R^1$ represents pyridyl, pyridazinyl, quinolinyl or isoquinolinyl, which monocyclic or bicyclic heterocyclic group is optionally substituted one or more times with substitutents selected from the group consisting of alkyl, alkoxy, cycloalkoxy, alkoxyalkoxy, alkoxyalkenyl, alkoxyalkynyl, alkynyl, alkenyl, alkenylthio, alkylseleno, alkoxycycloalkyl, hydroxyalkoxy, alkylthio, arylalkylthio, alkenoxy, alkynoxy, carboxylamido, arylthio, hydroxy, trifluoromethanesulfonyloxy, halogen; phenyl; phenyl substituted with alkyl, alkoxy, hydroxy, amino, or nitro; a pyrrolinyl, a piperidinyl, a tetrahydropyridyl, or a morpholinyl group, or, when $R^1$ is shown with two valences, $R^1$ is a divalent bridging radical derived by removal of a hydrogen atom from one of the groups listed in this definition of $R^1$; and "—R—B—R—" in Formula II represents a single bond bridge or a bridging group of the formula "—R—R—" or a bridging group of the formula "—R—"; or "—R—B—R$^1$—" or "—R—B—" in Formula IV represents a single bond bridge; or "—R—B—R$^1$—" in Formula III represents a single bond bridge or a bridging group of the formula "—R$^1$—R$^1$—" or a bridging group of the formula "—R$^1$—"; or "—R—B—R—" in Formula IV represents a single bond bridge or a bridging group of the formula "—R$^1$—R—"; or "—R$^1$—B—" in Formula IV represents a single bond bridge; and B represents a single bond bridge or a bridging element of the formula "—ALK—", "—ALK—X—ALK—", "—X—ALK—X—", "—PHE—", "—X—PHE—X—", or "—ALK—PHE—ALK—"; wherein "ALK" represents a single bond bridge or alkylene, alkenylene, or alkynylene; and "PHE" represents a phenylene group; and X represents O, S, NH, N-alkyl, or Se.

2. The diazacycloalkane of claim 1, wherein $R^1$ represents a member selected from the group consisting of
5-(1-heptynyl)-3-pyridyl;
5-(1-hexynyl)-3-pyridyl;
5-(1-pentynyl)-3-pyridyl;
5-(1-butynyl)-3-pyridyl;
5-(1-propynyl)-3-pyridyl;
5-methylseleno-3-pyridyl;
5-ethylseleno-3-pyridyl;
5-propylseleno-3-pyridyl;
5-butylseleno-3-pyridyl;
5-(pyrrolin-2-yl)-3-pyridyl;
5-(pyrrolin-3-yl)-3-pyridyl;
5-[N-(1,4,5,6-tetrahydropyridyl)]-3-pyridyl;
5-[N-(1,2,5,6-tetrahydropyridyl)]-3-pyridyl;
5,6-dibromo-3-pyridyl;
5-bromo-6-chloro-3-pyridyl;
6-bromo-5-chloro-3-pyridyl;
6-bromo-3-pyridyl;
5,6-dichloro-3-pyridyl;
6-fluoro-3-pyridyl;
6-iodo-3-pyridyl;
5-chloro-6-fluoro-3-pyridyl;
5-chloro-6-iodo-3-pyridyl;
5-bromo-6-fluoro-3-pyridyl;
5-bromo-6-iodo-3-pyridyl;
6-fluoro-pyridazinyl;
6-iodopyridazinyl;
5-pentyloxy-3-pyridyl;
5-(trans-hex-2-en-1-yl-oxy)-3-pyridyl;
5-butoxy-3-pyridyl;
5-methoxy-3-pyridyl;
5-propyloxy-3-pyridyl;
5-epoxy-3-pyridyl;
5-(2-ethyl-1-butoxy)-3-pyridyl;
5-(1-methyl-1-prop-2-en-oxy)-3-pyridyl;
5-(hex-2-en-oxy)-3-pyridyl;
5-(2-methyl-1-prop-1-en-oxy)-3-pyridyl;
5-(1-piperidinyl)-3-pyridyl; and
5-(1-morpholinyl)-3-pyridyl.

3. The diazacycloalkane of Formula III of claim 1, wherein "—R$^1$—B—R$^1$—" represents a single bond bridge or a bridging group of the formula "—R$^1$—R$^1$—" or a bridging group of the fomrula "—R$^1$—"; or B is a bridging group of the formula "—X—ALK—X—", wherein "ALK" represents $C_{1-4}$-alkylene; or B is a bridging group of the formula "—ALK—PHE—ALK—", wherein "ALK" represents $C_{1-4}$-alkylene, and "PHE" represents a phenylene group.

4. The diazacycloalkane of claim 1, said compound being 3,5-bis-(N,N'-homopiperazinyl)-pyridine;
1,4-[α,α'-Bis-(5-Ethoxy-3-pyridyl-1-homopiperazinyl)]-dimethylbenzene;
1,4-[α,α'-Bis-(6-Chloro-3-pyridazinyl-1-homopiperazinyl)]-dimethylbenzene;
O,O'-Bis-[5-(1-homopiperazinyl)-3-pyridyl]-ethyleneglycol; or
Homopiperazinyl-5-pyrid-3-yl-5-pyrid-3-yl-homopiperazine;
any of its enantiomers or any mixture thereof, an N oxide thereof, a pharmaceutically acceptable salt thereof, in a labelled or un-labelled form.

5. A pharmaceutical composition comprising a therapeutically-effective amount of a diazacycloalkane of claim 1, or a pharmaceutically-acceptable addition salt thereof, together with at least one pharmaceutically-acceptable carrier or diluent.

6. A method of treatment of withdrawal symptoms responsive to the activity of nAChR modulators, caused by termination of use of an addictive substance of a living animal body, including a human, comprising the step of administering to such a living animal body, including a human, in need thereof a therapeutically effective amount of the diazacycloalkane of claim 1.

7. The method according to claim 6, wherein said addictive substance is tobacco.

* * * * *